United States Patent
Bellis et al.

(10) Patent No.: US 8,976,367 B2
(45) Date of Patent: *Mar. 10, 2015

(54) STRUCTURED LIGHT 3-D MEASUREMENT MODULE AND SYSTEM FOR ILLUMINATING A SUBJECT-UNDER-TEST IN RELATIVE LINEAR MOTION WITH A FIXED-PATTERN OPTIC

(75) Inventors: Matthew W. Bellis, Lexington, KY (US); Daniel L. Lau, Lexington, KY (US)

(73) Assignee: Seikowave, Inc., Lexington, KY (US)

( * ) Notice: Subject to any disclaimer, the term of this patent is extended or adjusted under 35 U.S.C. 154(b) by 82 days.

This patent is subject to a terminal disclaimer.

(21) Appl. No.: 13/297,246

(22) Filed: Nov. 15, 2011

(65) Prior Publication Data

US 2012/0120413 A1 May 17, 2012

Related U.S. Application Data

(60) Provisional application No. 61/413,969, filed on Nov. 15, 2010.

(51) Int. Cl.
| | | |
|---|---|---|
| *G01B 11/24* | (2006.01) | |
| *G01B 11/25* | (2006.01) | |
| *G01N 21/956* | (2006.01) | |

(52) U.S. Cl.
CPC ........ *G01B 11/2513* (2013.01); *G01B 11/2536* (2013.01); *G01B 11/2545* (2013.01); *G01N 21/95684* (2013.01)
USPC .......................................... 356/603; 356/601

(58) Field of Classification Search
USPC ................. 356/601–608, 610–611, 616–618; 348/50, 46, E13.074
See application file for complete search history.

(56) References Cited

U.S. PATENT DOCUMENTS

| | | |
|---|---|---|
| 5,633,755 A | 5/1997 | Manabe et al. |
| 6,788,210 B1 | 9/2004 | Huang et al. |

(Continued)

OTHER PUBLICATIONS

Texas Instruments, DLP System Optics, Application Report DLPA022-Jul. 2010.*

(Continued)

*Primary Examiner* — Tri T Ton
(74) *Attorney, Agent, or Firm* — Macheledt Bales LLP

(57) ABSTRACT

A surface measurement module for 3-D triangulation-based image acquisition of a subject-under-inspection and under observation by at least one camera. The module having: (a) casing housing an optical system comprising a plurality of lens elements positioned between a fixed-pattern optic and a light source; (b) an output of said fixed-pattern optic comprising a multi-frequency pattern comprising a plurality of pixels representing at least a first and second superimposed sinusoid projected simultaneously, each of the sinusoids represented by the pixels having a unique temporal frequency and each of the pixels projected to satisfy $$I_n^p = A^p + \sum_{k=1}^{K} B_k^p \cos\left(2\pi f_k y^p + \frac{2\pi k n}{N}\right) \quad \text{Eq. (1.1)}$$

(c) the subject-under-inspection and fixed-pattern optic in relative linear motion during projection onto the subject-under-inspection of the output of the fixed-pattern optic; and (d) plurality of images captured of this output during projection onto the subject-under-inspection are used for the image acquisition.

10 Claims, 8 Drawing Sheets

(56) References Cited

U.S. PATENT DOCUMENTS

| | | | |
|---|---|---|---|
| 6,874,894 B2 | 4/2005 | Kitamura | |
| 6,977,732 B2 | 12/2005 | Chen et al. | |
| 7,440,590 B1 | 10/2008 | Hassebrook et al. | |
| 7,844,079 B2 | 11/2010 | Hassebrook et al. | |
| 8,224,068 B2 | 7/2012 | Hassebrook et al. | |
| 2010/0195114 A1 | 8/2010 | Mitsumoto et al. | |
| 2012/0092463 A1* | 4/2012 | Liu et al. | 348/50 |
| 2012/0113229 A1 | 5/2012 | Hassebrook et al. | |
| 2012/0120412 A1* | 5/2012 | Bellis et al. | 356/603 |

OTHER PUBLICATIONS

Liu, K., Y. Wang, D. L. Lau, Q. Hao, and L. G. Hassebrook, Dual-frequency pattern scheme for high-speed 3-D shape measurement, vol. 18, No. 5, Optics Express 5229-5244 (Mar. 1, 2010).

Wang, Y, K. Liu, D. L. Lau, and L. G. Hassebrook, Period Coded Phase Measuring Strategy for 3-D Realtime Acquisition and Data Processing, J. Opt. Soc. (2009).

Liu, K., Y. Wang, D. L. Lau, Q. Hao, and L. G. Hassebrook, LUT-based processing for structured light illumination real-time phase and 3-D surface reconstruction, J. Opt. Soc. (2009).

Li, Jielin, Hassebrook, L. G., and Guan, C., "Optimized two-frequency phase-measuringprofilometry light-sensor temporal-noise sensitivity," J. Opt. Soc. Am. A, vol. 20, No. 1, pp. 106-115 (Jan. 2003).

Frisken, S. F., R. N. Perry, A. P. Rockwood, and T. R. Jones, "Adaptively sampled distance fields: A general representation of shape for computer graphics," in Proceedings of the 27th annual conference on Computer graphics and interactive techniques, 249-254 (2000).

* cited by examiner

Figure 3
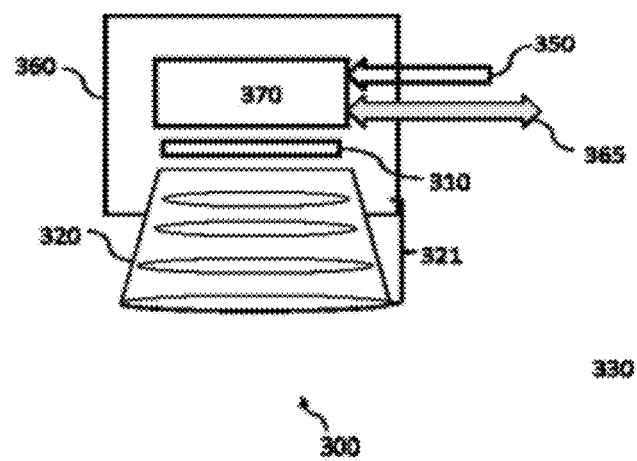
Figure 4
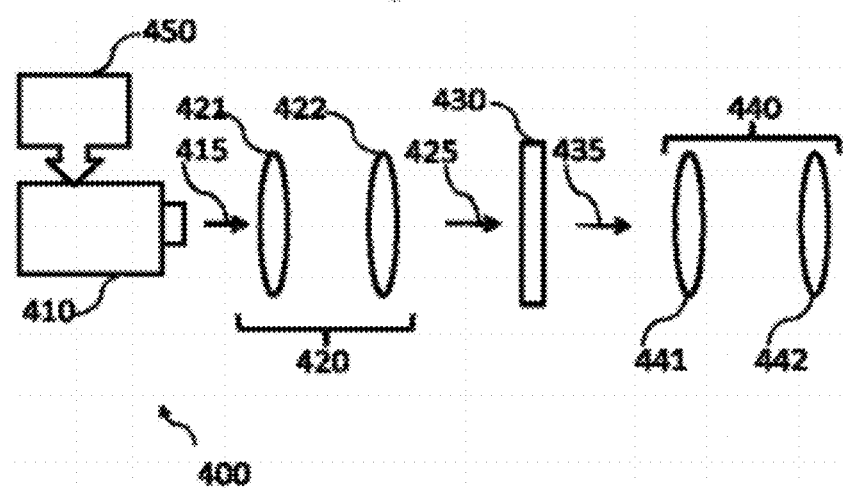
Figure 5.1A
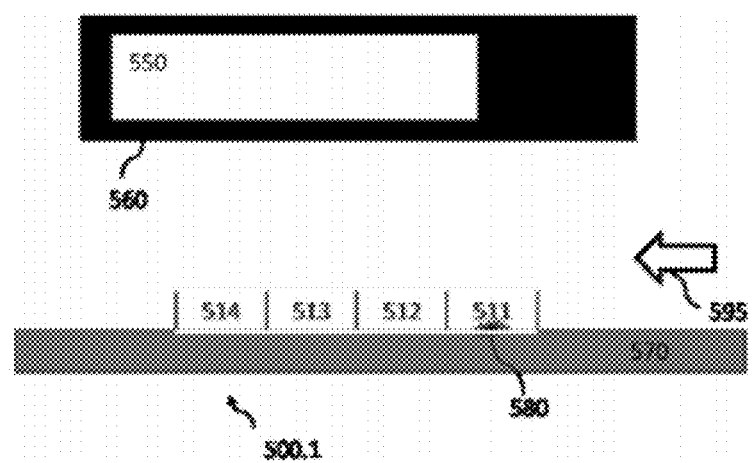

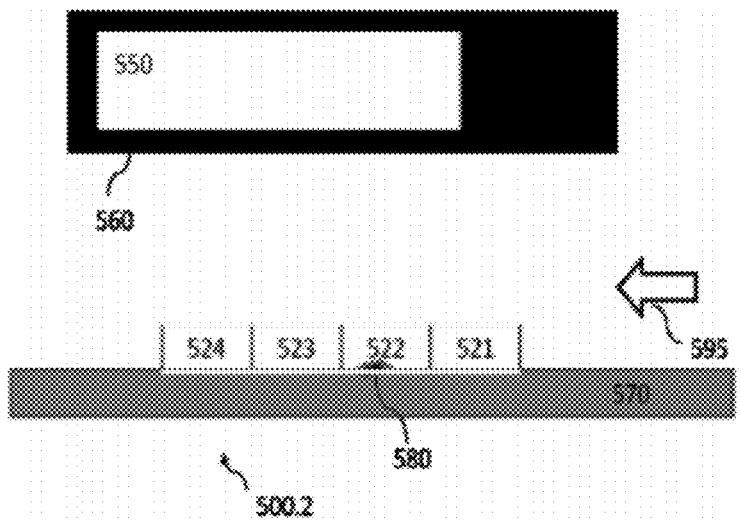
Figure 5.2A
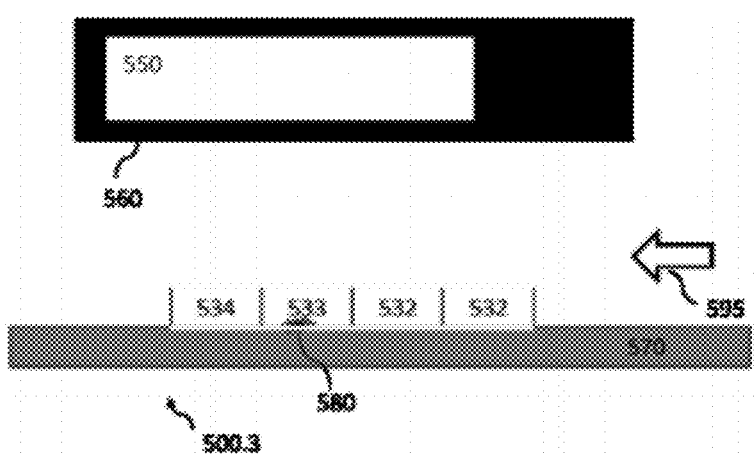
Figure 5.3A
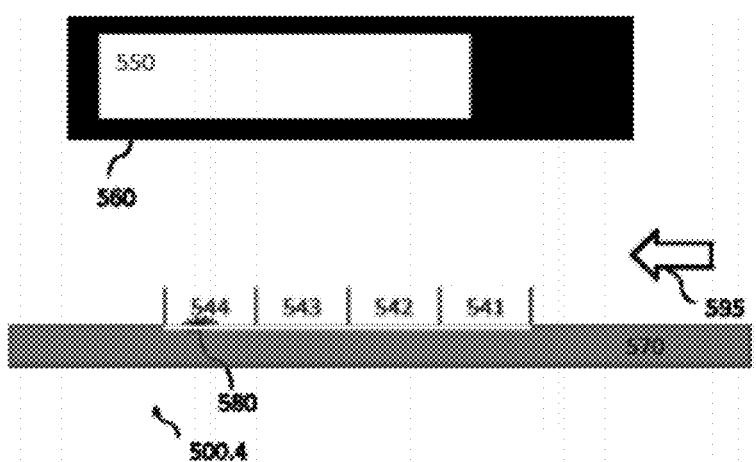
Figure 5.4A

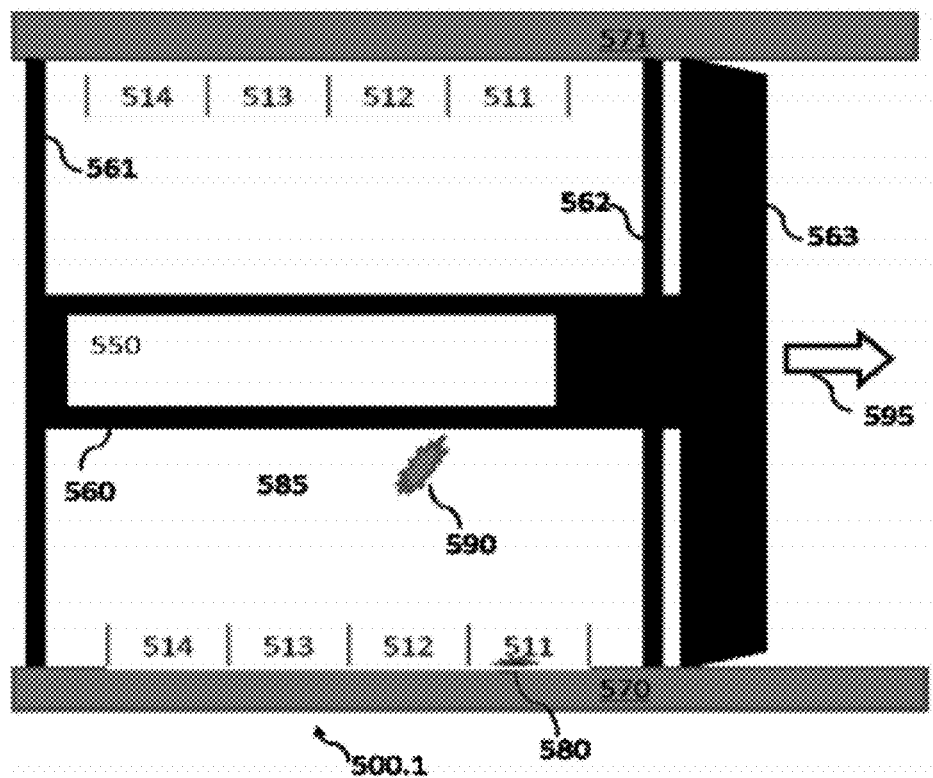
Figure 5.1B
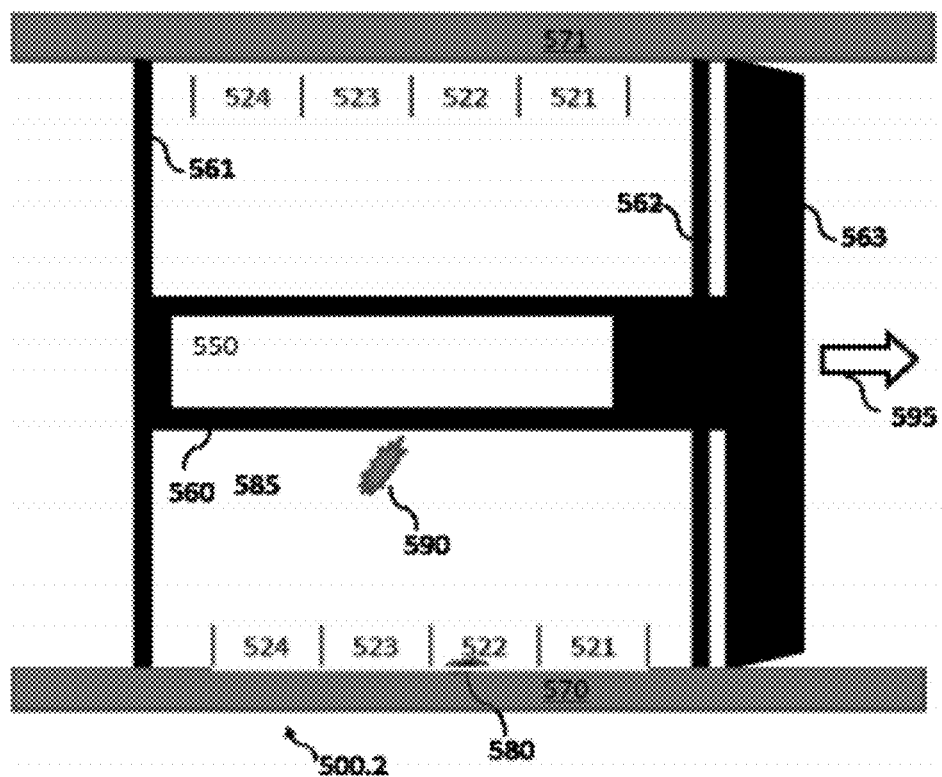
Figure 5.2B

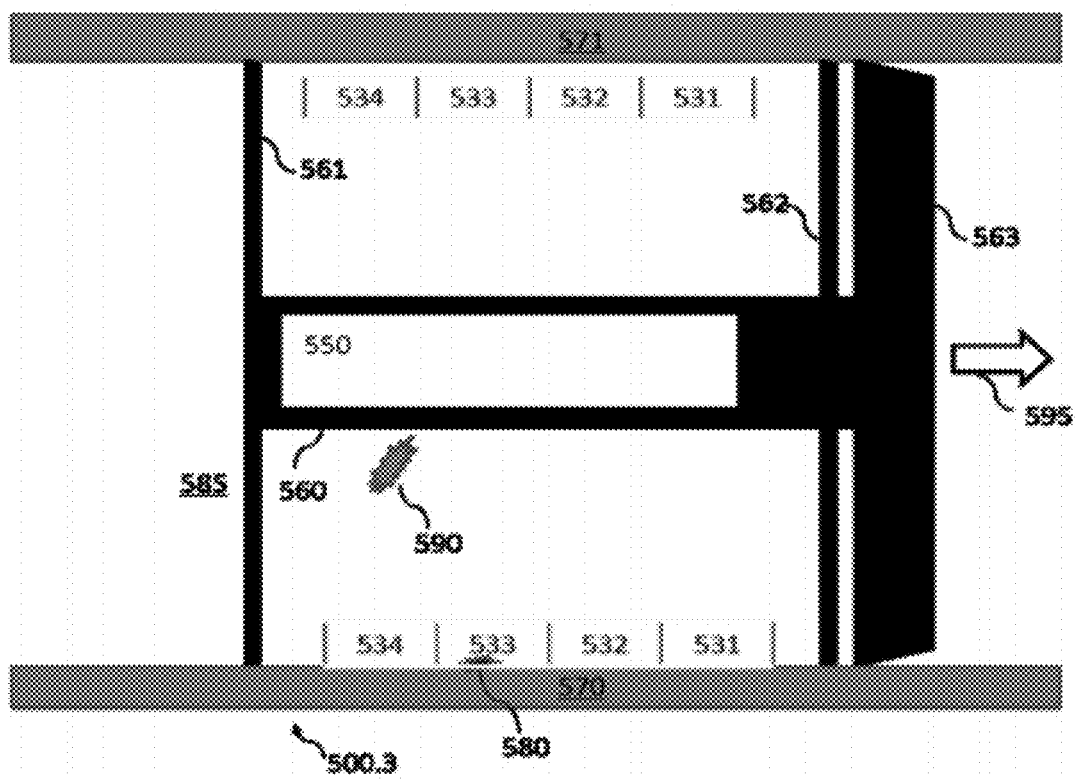
Figure 5.3B
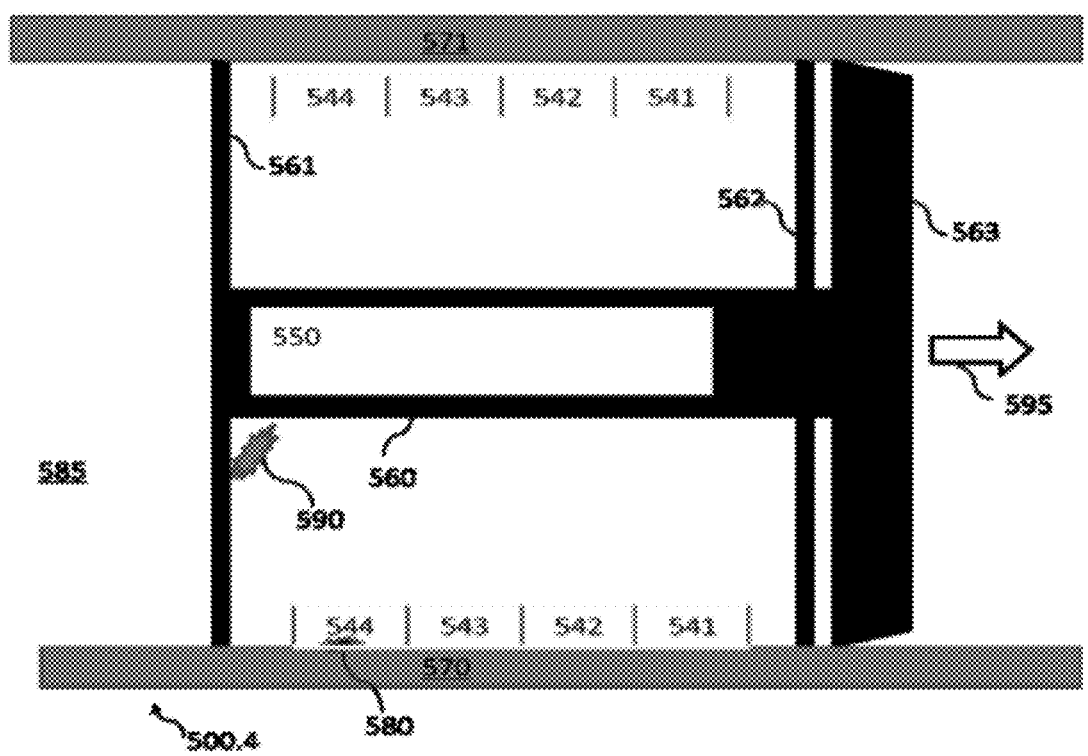
Figure 5.4B

STRUCTURED LIGHT 3-D MEASUREMENT MODULE AND SYSTEM FOR ILLUMINATING A SUBJECT-UNDER-TEST IN RELATIVE LINEAR MOTION WITH A FIXED-PATTERN OPTIC

CROSS REFERENCE TO RELATED APPLICATIONS

This application claims benefit under 35 U.S.C. 119(e) of U.S. Provisional Application No. 61/413,969 filed 15 Nov. 2010 by the applicants on behalf of the assignee, the complete disclosure of which—including attached materials—is incorporated herein by reference, to the extent the disclosure provides support and further edification hereof.

FIELD OF THE INVENTION

In general, the invention relates to the field of three-dimensional (3-D) measurement of surfaces using structured light illumination (SLI) techniques. Herein, "SLI" is used to represent the terms Structured Light Illumination, or often referred to, simply, as Structured Light. More-particularly, the invention is directed to the use of a new optical technique and system to measure and record the 3-D dimensional characteristics of 3-D surfaces of an object-under-test in relative linear motion with the measurement apparatus by projecting a selected superimposed SLI pattern composed of a plurality of SLI patterns, through a fixed-pattern optic, to illuminate a surface of interest of the area/object-under-test in motion. Furthermore, the invention is directed to a novel SLI inspection system of objects or items moving in a predictable linear fashion with respect to the inspection device, for example: for use along the interior of a pipeline (the measurement module moves linearly with respect to the interior surface of the pipeline-under-test); over semiconductor wafers undergoing fabrication along an assembly line, printed circuit board (PCB) or printed wiring board (PWB) defect inspection while the boards are moving on a conveyor belt, and other such surface inspection of a good or product-of-manufacture (parts, assemblies, foodstuff, packaging) traveling along a conveyor belt or assembly.

BACKGROUND OF THE INVENTION

Historical Perspective

The object measurement technique referred to as Structured Light (or, SLI) has been in use for measuring the 3-D characteristics of objects for many years. However, current implementations are computationally heavy and available systems have large footprints. Because conventional SLI surface measuring systems employ sophisticated electronically-driven SLI signal processing projection units to project SLI patterns—with each SLI pattern projected requiring a dedicated projector unit—it has been impractical to employ conventional SLI surface measuring systems to perform real-time measurements to monitor surfaces located in relatively small spaces (volumes), such as, surfaces located: inside the mouth or ear of a mammal (intra-oral and intra-aural surfaces), inside machinery (for example, machinery found in manufacturing plants); within a pipeline, and so on. Furthermore, the nature of projecting multiple sophisticated SLI patterns requisite for making 3-D surface measurements— where each conventional SLI pattern projected requires a dedicated projector unit—has further led way from the application of conventional SLI surface measuring systems to make real-time measurements of 3-D surfaces.

Structured Light (i.e., Structured Light Illumination), confocal imaging, time-of-flight, and parallel confocal microscopy are each considered 3-D measurement techniques. SLI is currently used to observe a surface-of-interest by projecting multiple SLI patterns (grid, stripes, ellipical patterns, and so on) with a projector onto a surface-of-interest while measuring, with a camera (lens and processing unit) the image reflected off the surface-of-interest to deduce resultant distortions of the patterns produced on the surface-of-interest. Knowing camera and projector geometry (many conventional techniques exists for such mapping), point-by-point depth information about the surface distortions is calculated by way of triangulation. World coordinates to camera are calculated using conventional well known mapping techniques such as that found at vision.caltech.edu/bouguetj/calib_doc/: "This toolbox works on Matlab 5.x, Matlab 6.x and Matlab 7.x on Windows, Unix and Linux systems and does not require any specific Matlab toolbox (for example, the optimization toolbox is not required)." Using the conventional camera calibration toolbox for Matlab, one computes the necessary coefficients to map world coordinates onto the coordinate system of the camera and the projector. In this manner, a mathematical relationship is defined between the camera (i.e., each individual pixel in the camera), the projector, (i.e., the origin of projected rows of information), and an object-under-test located in an external frame of reference, often referred to as the 'real world' coordinate system.

U.S. Pat. No. 6,788,210 entitled "METHOD AND APPARATUS FOR THREE DIMENSIONAL SURFACE CONTOURING AND RANGING USING A DIGITAL VIDEO PROJECTION SYSTEM," uses a complex series of interconnected dedicated projector units engaged to generate a desired projected multi-pattern image on a surface of interest; FIG. 5 from U.S. Pat. No. 6,788,210 illustrates one conventional optical configuration for a projection system. U.S. Pat. No. 5,633,755 provides additional detail regarding the configuration of an optical system and its electronic control system. U.S. Pat. No. 6,874,894 B2 entitled "DMD EQUIPPED PROJECTOR" details a system known as "Texas Instruments DMD" projector, i.e., the 'DLP device' of a projection apparatus.

As one can appreciate, the system depicted in FIG. 5 from U.S. Pat. No. 6,788,210 and the system depicted in FIG. 5 of U.S. Pat. No. 6,874,894 are structurally and functionally the same. As explained in U.S. Pat. No. 6,788,210, to generate an image, component 46 is used. This component has been labeled 113 in FIG. 6 of U.S. Pat. No. 6,874,894 B2 as PRIOR ART. The Texas Instruments DMD, also known as the DMD or the DLP device, is an complicated semiconductor device, specifically referred to as an optical MEMS device. The DMD is further detailed in Hornbeck, Larry J., "*Digital Light Processing for High-Brightness, High-Resolution Applications,*" SPIE Vol. 3013 pps. 27-40; by way of background only, the content found on the Internet at the domain dlp.com.

U.S. Pat. No. 6,977,732 describes an application of the DMD to measure the three dimensional shape of small objects. As explained therein, additional complex electronic systems are needed to operate the DMD-based projection system: It has an electronic micro-display for three dimensional measurements. Seiko-Epson manufactures liquid crystal devices for projection applications. Sony, Omnivision, and JVC each manufacture liquid crystal on silicon devices for projection applications. Like the DMD, conventional devices are electronically-controlled so that projection of light patterns requires complicated optical control electronics and optics structures.

Computerized Devices, Memory and Storage Devices/Media

I. Digital computers. A processor is the set of logic devices/circuitry that responds to and processes instructions to drive a computerized device. The central processing unit (CPU) is considered the computing part of a digital or other type of computerized system. Often referred to simply as a processor, a CPU is made up of the control unit, program sequencer, and an arithmetic logic unit (ALU)—a high-speed circuit that does calculating and comparing. Numbers are transferred from memory into the ALU for calculation, and the results are sent back into memory. Alphanumeric data is sent from memory into the ALU for comparing. The CPUs of a computer may be contained on a single 'chip', often referred to as microprocessors because of their tiny physical size. As is well known, the basic elements of a simple computer include a CPU, clock and main memory; whereas a complete computer system requires the addition of control units, input, output and storage devices, as well as an operating system. The tiny devices referred to as 'microprocessors' typically contain the processing components of a CPU as integrated circuitry, along with associated bus interface. A microcontroller typically incorporates one or more microprocessor, memory, and I/O circuits as an integrated circuit (IC). Computer instruction(s) are used to trigger computations carried out by the CPU.

II. Computer Memory and Computer Readable Storage. While the word 'memory' has historically referred to that which is stored temporarily, with storage traditionally used to refer to a semi-permanent or permanent holding place for digital data—such as that entered by a user for holding long term—however, the definitions of these terms have blurred. A non-exhaustive listing of well known computer readable storage device technologies compatible with a variety of computer processing structures are categorized here for reference: (1) magnetic tape technologies; (2) magnetic disk technologies include floppy disk/diskettes, fixed hard disks (often in desktops, laptops, workstations, host computers and mainframes interconnected to create a 'cloud' environment, etc.), (3) solid-state disk (SSD) technology including DRAM and 'flash memory'; and (4) optical disk technology, including magneto-optical disks, PD, CD-ROM, CD-R, CD-RW, DVD-ROM, DVD-R, DVD-RAM, WORM, OROM, holographic, solid state optical disk technology, etc.

BACKGROUND OF THE INVENTION

Use of Multi-Frequency Patterns

The instant new technique and system disclosed herein, leverage the unique technique disclosed in U.S. Provisional Patent Application 61/371,626, Liu et al., filed 6 Aug. 2010 entitled "Dual-frequency Phase Multiplexing (DFPM) and Period Coded Phase Measuring (PCPM) pattern strategies in 3-D structured light systems, and Lookup Table (LUT) based real-time data processing for phase measuring pattern strategies," fully incorporated herein by reference for its technical background discussion. U.S. utility application Ser. No. 13/205,607, Liu et al., filed 8 Aug. 2011 ("Util App '607") was granted priority to U.S. Provisional Patent Application 61/371,626, Liu et al. ("Provisional Application '626"): the technical disclosures of both Provisional Application '626 and Util App '607 are hereby fully incorporated herein by reference to the extent consistent with the instant technical specification. While Provisional Application '626 and Util App '607 were commonly owned upon filing of the latter, neither Provisional Application '626 or Util App '607 is commonly owned by the assignee of the instant patent application. The unique SLI patterning technique disclosed in Provisional Application '626 and Util App '607 comprises:

(1) a unique pattern strategy component (further detailed in technical discussions found in Provisional Application '626 as labeled Section A. "Dual-frequency pattern scheme for high-speed 3-D shape measurement" and as labeled Section B. "Period Coded Phase Measuring Strategy for 3-D Realtime Acquisition and Data Processing"—each of these Sections A. and B. covers an example of a new multi-frequency pattern introduced by way of analogy to the following two traditional electrical circuitry signal/current propagation types: AC, alternating current, and DC, direct current, as further explained below); and (2) a unique de-codification image processing component (further detailed in the technical discussion of Provisional Application '626 and labeled Section C. "LUT-based processing for structured light illumination real-time phase and 3-D surface reconstruction").

As noted above and detailed further in Provisional Application '626 and Util App '607, the two examples set forth in Sections A. and B. of the new multi-frequency patterns disclosed in Provisional Application '626 were introduced in terms of analogies to traditional electrical circuitry signal/current propagation types: An AC flavor and DC flavor. These same Sections A. and B. were integrated into applicants' Provisional Application No. 61/413,969 filed 15 Nov. 2010, incorporated herein by reference as noted above. The multi-frequency pattern detailed in Section A. fashioned after principals governing AC electrical systems was coined "Dual-frequency Phase Multiplexing" (DFPM). As noted in applicants' Provisional Application No. 61/413,969, the material in Section A. was earlier published as 1 Mar. 2010/Vol. 18, No. 5/Optics Express 5233 and is noted in the section of Util App '607 labeled EXAMPLE 01. The multi-frequency pattern detailed in Section B. fashioned after principals governing DC electrical systems was coined "Period Coded Phase Measuring" (PCPM). Dual-frequency Phase Multiplexing (DFPM) patterns comprise two superimposed sinusoids, one a unit-frequency phase sine wave and the other a high-frequency phase sine wave, whereby after receiving/acquiring the pattern data by an image sensor, the phase of the two patterns is separated. The unit-frequency phase is used to unwrap the high-frequency phase. The unwrapped high-frequency phase is then employed for 3-D reconstruction. Period Coded Phase Measuring (PCPM) patterns—fashioned after DC current propagation—are generated with the period information embedded directly into high-frequency base patterns, such that the high-frequency phase can be unwrapped temporally from the PCPM patterns.

As explained in Util App '607—the specification of which is quoted extensively below—using unique multi-frequency patterns, the '607 technique accomplishes:

3-D triangulation-based image acquisition of a contoured surface-of-interest (or simply, "contour" or "contour-of-interest") under observation by at least one camera, by projecting onto the surface-of-interest a multi-frequency pattern comprising a plurality of pixels representing at least a first and second superimposed sinusoid projected simultaneously, each of the sinusoids represented by the pixels having a unique temporal frequency and each of the pixels projected to satisfy $$I_n^p = A^p + \sum_{k=1}^{K} B_k^p \cos\left(2\pi f_k y^p + \frac{2\pi k n}{N}\right) \quad \text{Eq. (1.1)}$$

where $I_n^p$ is the intensity of a pixel in the projector for the $n^{th}$ projected image in a particular instant/moment in time (p, to represent projector); K is an integer representing the number of component sinusoids (e.g., K=2 for a dual-frequency sinusoid pattern, K=3 for a triple-frequency sinusoid, and so on), each component sinusoid having a distinct temporal frequency, where K≤(N+1)/2. The parameter $B_k^p$ represents constants that determine the amplitude or signal strength of the component sinusoids; $A^p$ is a scalar constant used to ensure that all values of $I_n^p$ are greater than zero, 0 (that is to say, that the projector unit will not project less than 0 magnitude of light); $f_k$ is the spatial frequency of the $k^{th}$ sinusoid corresponding to temporal frequency k; and $y^p$ represents a spatial coordinate in the projected image. For example, $y^p$ may represent a vertical row coordinate or a horizontal column coordinate of the projected image; n represents phase-shift index or sequence order (e.g., the n=0 pattern is first projected, and then the n=1 pattern, and so on, effectively representing a specific moment in discrete time). N is the total number of phase shifts—i.e., the total number of patterns—that are projected, and for each pattern projected, a corresponding image will be captured by the camera (or rather, the camera's image sensor). When used throughout, the superscript "c" references parameters relating to an image or series of images (video) as captured by the camera, whereas superscript "p" references the projector.

Where pixels are projected to satisfy Eq. 1.1, the pixels of the images then captured by the camera are defined according to the unique technique governed by the expression:

$$I_n^c = A^c + \sum_{k=1}^{K} B_k^c \cos\left(2\pi f_k y^p + \frac{2\pi k n}{N}\right) + \eta \quad \text{Eq. (1.2)}$$

The term η ("eta") represents a noise due to a certain amount of error introduced into the image by the light sensor of the camera. Recall, a camera image is made up of a multitude of pixels, each pixel defined by Eq. 1.2, with values for $A^c$, $B_k^c$, and $\eta^c$ different for each pixel. The "c" superscript indicating a value is dependent on the position of the pixel as referenced in the camera sensor ('camera space'). To obtain phase terms from the pixels projected in accordance with Eq. 1.2, the unique expression, below, is carried-out for each k:

$$2\pi f_k y^p = \arctan\left(\frac{\sum_{n=0}^{N-1} I_n^c \times \cos\left(\frac{2\pi k n}{N}\right)}{\sum_{n=0}^{N-1} I_n^c \times \sin\left(\frac{2\pi k n}{N}\right)}\right) \quad \text{Eq. (1.3)}$$

where, as before, $y^p$ represents a spatial coordinate in the projected image. In EXAMPLE 01, herein below, where K is set equal to 2, the phase terms for the cases where k=1 and k=2 (i.e., for the two superimposed sinusoids) must be determined. FIGS. 8A, 8B are reproductions of computer-generated/implemented images; FIG. 8C is FIG. 8B, enlarged to view representative stripes numbered from the top 1 through 10, by way of example. FIG. 8A is an image representing phase for the k=1 term where f=1 (unit-frequency). FIGS. 8B, 8C are reproductions of an image representing the phase term for k=2 where f=20 (i.e., the high-frequency sinusoid). Note that the stripped pattern in FIGS. 5B/C has 20 stripes.

When applying the use of temporal unwrapping techniques, for the case where k=2 using Eq. 1.1, one can determine that the projected pixels will satisfy $$I_n^p = A^p + B_2^p \cos\left(2\pi f_2 y^p + \frac{2\pi 2 n}{N}\right), k=2 \quad \text{Eq. (1.1)}$$

Where this leads to 20 stripes (as shown, for example, in FIG. 8B as a pattern projected on a human hand, the enlargement of which is labeled FIG. 8C to better view stripes), one must determine which of the 20 stripes each particular pixel falls in the projected image (e.g., FIG. 8C). Using a traditional phase unwrapping approach to determine where each pixel fell in the projected image would require a mathematical form of 'stripe counting'—which is computationally quite burdensome.

Rather, according to the instant invention, a second set of patterns (k=1) all unit-frequency sinusoids (i.e., f=1) is superimposed with a high-frequency sinusoid, such as one of 20 stripes, k=2 pattern. The unit-frequency signal is defined by an adaptation of Eq. 1.1

$$I_n^p = A^p + B_1^p \cos\left(2\pi f_2 y^p + \frac{2\pi n}{N}\right), k=1 \quad \text{Eq. (1.1)}$$

Therefore, rather than projecting a total of N patterns onto the contoured surface-of-interest, there are now 2*N patterns projected (such that K=2 and each pixel projected from the projector is comprised of a dual-frequency pattern, one is a unit-frequency sinusoid and the second is a high-frequency sinusoid). However, very unique to the applicants' technique according to the invention, the plurality of pixels projected using Eq. 1.1 are 'instantly decodable' such that the computerized processing unit (CPU) of the computerized device in communication with the projector and camera units, at this point already, has the data and the means to determine (closely enough) which stripe each projected pixel $I_n^p$ is in, while determining $2\pi f_2 y^p$ (i.e., phase) of the camera image (of pixel intensity, $I_n^c$), according to Eq. 1.3—reproduced again, below, for handy reference:

$$2\pi f_k y^p = \arctan\left(\frac{\sum_{n=0}^{N-1} I_n^c \times \cos\left(\frac{2\pi k n}{N}\right)}{\sum_{n=0}^{N-1} I_n^c \times \sin\left(\frac{2\pi k n}{N}\right)}\right) \quad \text{Eq. (1.3)}$$

To carry-out phase unwrapping of the high-frequency sinusoid the following steps can be taken:

$$unitPhase = \arctan\left(\frac{\cos\Sigma K_1}{\sin\Sigma K_1}\right)$$

-continued $$highPhase = \arctan\left(\frac{\cos\Sigma K_2}{\sin\Sigma K_2}\right)/f_2$$

$$tempPhase = \text{round}\left(\frac{(unitPhase - highPhase)}{(2\pi)f_2}\right)$$

$$finalPhase = tempPhase + highPhase*(2\pi/f_2).$$

Or, summarized in pseudo code short-hand notation as done in FIG. 19, the above computational steps may be rewritten as:
  unitPhase=arctan(cosSumK1/sinSumK1);
  highPhase=arctan(cosSumK2/sinSumK2)/F2;
  tempPhase=round((unitPhase-highPhase)/(2*PI)*F2);
  finalPhase=tempPhase+highPhase*2*PI/F2

The first and second superimposed sinusoid may comprise, for example as noted in EXAMPLE 01, below, a unit-frequency sinusoid (in this context, 'unit' refers to having a magnitude value of 1) superimposed on a high-frequency sinusoid, the unit-frequency sinusoid and high-frequency sinusoid being projected simultaneously (i.e., effectively 'on top of one another' over a selected epoch/duration of frames, n) from a projection unit, or projector, as a plurality of pixels such that each of the pixels projected satisfy the expression $$I_n^p = A^p + B_1^p \cos\left(2\pi f_h y^p - \frac{2\pi n}{N}\right) + B_2^p \cos\left(2\pi f_u y^p - \frac{4\pi n}{N}\right)$$

where $I_n^p$ is the intensity of a pixel in the projector, $A^p$, $B_1^p$, and $B_2^p$ are constants set such that the value of $I_n^p$ falls between a target intensity range, (e.g., between 0 and 255 for an 8-bit color depth projector), $f_h$ is the high frequency of the sine wave, $f_u$ is the 'unit' frequency of the sine wave. The unit-frequency signal/sinusoid is used during a demodulation step to produce a decodable, unwrapped-phase term temporally.

Additionally, the process includes a decoding of the projected patterns by carrying-out a lookup table (LUT)-based processing of video image data acquired by at least one image-capture device. The decoding step is performed to extract, real-time, coordinate information about the surface shape-of-interest. The LUT-based processing includes the step of implementing (or, querying) a pre-computed modulation lookup table (MLUT) to obtain a texture map for the contoured surface-of-interest and implementing (or, querying) a pre-computed phase lookup table (PLUT) to obtain corresponding phase for the video image data acquired of the contoured surface-of-interest. Furthermore, use of conventional digital image point clouds can be made to display, real-time, the data acquired.

In one aspect, the unique computer-implemented process, system, and computer-readable storage medium with executable program code and instructions, can be characterized as having two stages. The first being a dual-frequency pattern generation and projection stage, the dual-frequency pattern characterized by the expression $$I_n^p = A^p + B_1^p \cos\left(2\pi f_h y^p - \frac{2\pi n}{N}\right) + B_2^p \cos\left(2\pi f_u y^p - \frac{4\pi n}{N}\right)$$

where $I_n^p$ is the intensity of a pixel in the projector, $A^p$, $B_1^p$, and $B_2^p$ are constants that are preferably set, by way of example, to make the value of $I_n^p$ fall between 0 and 255 for an 8-bit color depth projector, $f_h$ is the high frequency of the sine wave, $f_u$ is the unit frequency of the sine wave and equals 1, n represents phase-shift index, and N is the total number of phase shifts and is preferably greater than or equal to 5. The second stage comprises a de-codification stage employing a lookup table (LUT) method for phase, intensity/texture, and depth data.

By way of using lookup tables (LUT) to obtain modulation (M) and phase (P) according to $$MLUT[U, V] = \frac{1}{3}[3V^2 + U^2]^{0.5} \text{ and}$$

$$PLUT[U, V] = \tan^{-1}\left[\frac{3^{0.5}V}{U}\right].$$

Next, a conversion of phase to X, Y, Z point clouds is implemented using the following:

$$Z^w = M_z(x^c, y^c) + N_z(x^c, y^c)T,$$
$$X^w = E_x(x^c, y^c)Z^w + F_x(x^c, y^c)$$
$$Y^w = E_y(x^c, y^c)Z^w + F_y(x^c, y^c)$$

where $$E_x(x^c, y^c) = \frac{(m_{22}^c m_{33}^c - m_{23}^c m_{32}^c)x^c + (m_{13}^c m_{32}^c - m_{12}^c m_{33}^c)y^c + (m_{12}^c m_{23}^c - m_{13}^c m_{22}^c)}{(m_{21}^c m_{32}^c - m_{22}^c m_{31}^c)x^c + (m_{12}^c m_{31}^c - m_{11}^c m_{32}^c)y^c + (m_{11}^c m_{22}^c - m_{12}^c m_{21}^c)},$$

$$F_x(x^c, y^c) = \frac{(m_{22}^c m_{34}^c - m_{24}^c m_{32}^c)x^c + (m_{14}^c m_{32}^c - m_{12}^c m_{34}^c)y^c + (m_{12}^c m_{24}^c - m_{14}^c m_{22}^c)}{(m_{21}^c m_{32}^c - m_{22}^c m_{31}^c)x^c + (m_{12}^c m_{31}^c - m_{11}^c m_{32}^c)y^c + (m_{11}^c m_{22}^c - m_{12}^c m_{21}^c)},$$

$$E_y(x^c, y^c) = \frac{(m_{23}^c m_{31}^c - m_{21}^c m_{33}^c)x^c + (m_{11}^c m_{33}^c - m_{13}^c m_{31}^c)y^c + (m_{13}^c m_{21}^c - m_{11}^c m_{23}^c)}{(m_{21}^c m_{32}^c - m_{22}^c m_{31}^c)x^c + (m_{12}^c m_{31}^c - m_{11}^c m_{32}^c)y^c + (m_{11}^c m_{22}^c - m_{12}^c m_{21}^c)}, \text{ and}$$

$$F_y(x^c, y^c) = \frac{(m_{21}^c m_{32}^c - m_{22}^c m_{31}^c)x^c + (m_{12}^c m_{31}^c - m_{11}^c m_{32}^c)y^c + (m_{11}^c m_{22}^c - m_{12}^c m_{21}^c)}{(m_{21}^c m_{32}^c - m_{22}^c m_{31}^c)x^c + (m_{12}^c m_{31}^c - m_{11}^c m_{32}^c)y^c + (m_{11}^c m_{22}^c - m_{22}^c m_{21}^c)}.$$

Implementing the 7 parameters $M_z$, $Z_z$, $C$, $E_x$, $E_y$, $F_x$, and $F_y$ by means of table look-up for indices ($x^c$, $y^c$) (camera column and row indices), reduces the total computational complexity associated with deriving the 3-D point cloud from the phase term to 7 look-ups. 4 additions. 3 . . . end quoted text from Util App '607 . . . .

The flow diagram FIG. 19 from Util App '607 summarizes Liu et al's technique 200 as quoted extensively immediately above. By way of example, the diagram FIG. 19 is incorporated herein and added and made part of the instant disclosure as FIG. 10; the technique of Liu et al. referenced at 1100 as PRIOR ART.

The compact module and system of the invention employs a light source 410, a plurality of lens elements 420 as well as 440, and a unique fixed-pattern optic 430 from which a superimposed/overlaid SLI pattern composed of a plurality of SLI patterns (for example, as shown in FIG. 6, 600 and FIG. 7, 710) is output 435 to illuminate a surface of a 3-D object/ subject-under-test or a 3-D area-under-inspection, as the case may be. The pixel intensity profile pattern (FIG. 6, 600 or FIG. 7, 710) fixed into the fixed-patterned optic 430 (FIG. 4) can be comprised of two sinusoids at least one of which is a unit-frequency sinusoid (i.e., having a magnitude value of 1) superimposed onto a high-frequency sinusoid, such that the unit-frequency sinusoid and high-frequency sinusoid are projected simultaneously over a selected epoch/duration of frames, n, such that each of the pixels projected satisfy the expression 650, FIG. 6 which is the same as expression 750, FIG. 7, and reproduced below. The expression, below, is likewise the same as that referred to as prior art eqn. (8) in Section A. of applicants' Provisional Application No. 61/413,969 and in Section A. of Provisional Application '626, as well as further explained in EXAMPLE 01 of Util App '607:

$$I_n^p = A^p + B_1^p \cos\left(2\pi f_h y^p - \frac{2\pi n}{N}\right) + B_2^p \cos\left(2\pi f_u y^p - \frac{4\pi n}{N}\right)$$

where $I_n^p$ is the intensity of a pixel in the projector, $A^p$, $B_1^p$, and $B_2^p$ are constants set such that the value of $I_n^p$ falls between a target intensity range, (e.g., between 0 and 255 for an 8-bit color depth projector), $f_h$ is the high frequency of the sine wave, $f_u$ is the 'unit' frequency of the sine wave. The unit-frequency signal/sinusoid is used during a demodulation step to produce a decodable, unwrapped-phase term temporally. Preferably, pixel intensity profile pattern 600 or 710 is 'fixed' into a transparent lens member, by way of etching into, depositing onto, or otherwise 'fixing' into the lens member, causing light entering the patterned optic 430, to exit as pattern light output 435, FIG. 4 having the pixel intensity profile pattern 600 or 710.

The unique compact measurement apparatus and system adapted to make high-resolution measurements in real-time, leverage off the SLI patterning technique detailed further in Provisional Application '626 and Util App '607 resulting in a unique.

SUMMARY OF THE INVENTION

One will appreciate the distinguishable features of the system and associated technique described herein from those of known 3-D shape recognition techniques, including any prior designs invented by one or more of the applicants hereof. Certain of the unique features, and further unique combinations of features—as supported and contemplated herein—may provide one or more of a variety of advantages, among which include: (a) ready integration and flexibility/versatility (i.e., use in a wide variety of environments to gather 3-D surface data about a multitude of different areas/subjects/objects-under-test); (b) single 'snap-shot' investigation of an area/subject/object-under-test and/or provide ongoing monitoring/investigation/test of an area/subject/object without disruption of the surface environment around the area/object/subject; and/or (c) speed of measurements and real-time results, particularly useful to minimize artifacts that may result from motion of an object or subject (e.g., mammal) that is in motion when surface data is measured.

BRIEF DESCRIPTION OF DRAWINGS

For purposes of illustrating the innovative nature plus the flexibility of design and versatility of the new system and associated technique, as customary, figures are included. One can readily appreciate the advantages as well as novel features that distinguish the instant invention from conventional computer-implemented tools/techniques. The figures as well as any incorporated technical materials have been included to communicate the features of applicants' innovation by way of example, only, and are in no way intended to limit the disclosure hereof.

FIG. 3 A high-level block diagram schematically illustrating a Camera system 300 for capturing an image of the illuminated Object/subject-under-test 570, as shown in FIGS. 5A and 5B.

FIG. 4 A high-level block diagram schematically illustrating Projection system architecture 400 having a Light source 410, optical system 420, Fixed-pattern optic 430 in communication with an Optic shifting element 431 and Projection optical system 440.

FIGS. 5.1A-5.4A High-level block diagrams schematically illustrating a Measurement module 550 (general case) in operation measuring, respectively, Area(s)-under-inspection 511-514, 521-524, 531-534, 541-544.

FIGS. 5.1B-5.4B Alternative embodiment of the Measurement module 550 wherein the Object-under-test 570, 571 comprises the inside wall of a pipeline or tubing (570, 571 representing cross-sections thereof), within which a fluid (non-compressible fluids, such as oil or water, or compressible fluids, such as natural gas) can flow.

DESCRIPTION DETAILING FEATURES OF THE INVENTION

Figure 1:
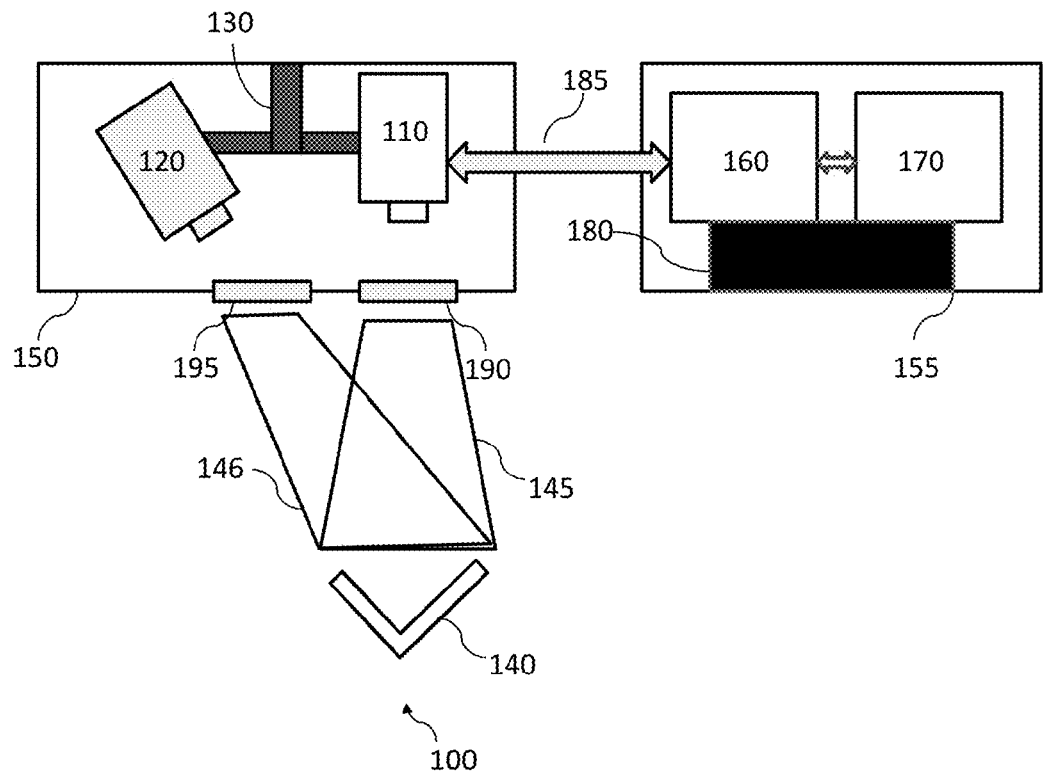
FIG. 1 A high-level block diagram schematically illustrating a Measurement module 100 having Measurement module thermal isolation chamber/case 150 enclosing a Projection system 110 and single camera system 120.

By viewing the figures, the technical reference materials incorporated by reference herein, one can further appreciate the unique nature of core as well as additional and alternative features of the new apparatus/module and associated system disclosed herein. Back-and-forth reference and association has been made to various features and components represented by, or identified in, the figures. While "FIG. 1" may be interchangeably referred to as "FIG. 1", as used throughout, either is intended to reference the same figure, i.e., the figure labeled FIG. 1 in the set of figures. Structural and functional details have been incorporated herein—by way of example only—to showcase the use of the compact module and system of the invention employing a light source 410, a plurality of lens elements 420 as well as 440, and a unique fixed-pattern optic 430 from which a superimposed/overlaid SLI pattern composed of a plurality of SLI patterns (for example, as shown in FIG. 6, 600 and FIG. 7, 710) is output 435 to illuminate a surface of a 3-D object/subject-under-test or a 3-D area-under-inspection, as the case may be.

Uniquely and according to the invention: Inspecting an Object-under-test using a 'fixed' SLI pattern optic 430 with relative linear motion between the measurement module and the Object-under-test, eliminates the conventional requirement of projecting multiple SLI patterns in time-sequential fashion at a surface of an object of interest. The projection system of the invention employs a fixed-pattern optic fabricated to project requisite superimposed SLI patterns, simultaneously, using a unique technique. In one preferred implementation (FIG. 6, 600), a four phase pattern comprised of strips (610, 620, 630, 640) of a core SLI pattern, is projected, in effect projecting four adjacent patterns 'simultaneously' at a surface of interest. The patterns are offset from each other spatially, FIG. 6, 600. A camera system 120, 220, 221 'simultaneously' inspects the entire projected area (intersection of areas defined by 145 and 146, FIG. 1, intersection of areas defined by 245 and 246, intersection of areas defined by 945 and 946). As the object under test moves, the portion of the object under test is time-sequentially illuminated by each of the projected patterns. In this manner, the camera can acquire the necessary pixel data which, when combined with the calibration data, enable calculation of the 3-D characteristics of the Object-under-test.

In addition, the velocity of the Object-under-test can be acquired, or retrieved, from the pixel data collected/measured with the camera. If the velocity changes during data acquisition, this can be detected and the change in the velocity incorporated—i.e., fed back—into the 3-D calculations to further improve the accuracy of the measurement.

Below is a list of components/features/assemblies shown and labeled throughout the Figures matching reference numeral with terms selected for the components/features/assemblies depicted:

| Reference numeral | component/feature description |
|---|---|
| 100 | Measurement module |
| 110 | Projection system |
| 120 | Single camera system |
| 130 | Measurement module mechanical mount |
| 140 | Calibration fixture |
| 145 | Projector illumination area |
| 146 | Camera field of view |
| 150 | Measurement module case |
| 155 | System controller and data storage case |
| 160 | System controller |
| 170 | Data storage |
| 180 | System controller and data storage mechanical mount |
| 185 | Control and data bus |
| 190 | Projector aperture |
| 195 | Camera aperture |
| 200 | Alternative measurement module |
| 210 | Projection system |
| 220 | First camera system |
| 221 | Second camera system |
| 230 | Measurement module mechanical mount |
| 240 | Calibration fixture |
| 245 | Projector illumination area |
| 246 | First camera field of view |
| 247 | Second camera field of view |
| 250 | Measurement module case |
| 255 | System controller and data storage case |
| 260 | System controller |
| 270 | Data storage |
| 280 | System controller and data storage mechanical mount |
| 285 | Control and data bus |
| 290 | Projector aperture |
| 295 | First camera aperture |
| 296 | Second camera aperture |
| 300 | Camera system architecture |
| 310 | Image sensor |
| 320 | Camera lens |
| 321 | Camera lens elements |
| 330 | Camera pixel data output format |
| 350 | Camera power unit |
| 360 | Camera mechanical frame |
| 365 | Camera pixel data output bus |
| 370 | Camera pixel data processing device |
| 400 | Projection system architecture |
| 410 | Light source (source of illumination) |
| 415 | Light output from light source |
| 420 | Illumination optical system |
| 421 | Illumination system lens element |
| 422 | a second illumination system lens element |
| 425 | Light output from light source shaped by upstream illumination system at 420 |
| 430 | Fixed-pattern optic structure (transparent support and etched-pattern layer) |
| 431 | Optic shifting element (shifts, or reorients, fixed-pattern optic structure at 430) |
| 435 | Patterned light output |
| 440 | Projection optical system |
| 441 | Projection system lens element |
| 442 | a second projection system lens element |
| 450 | Projector power unit |
| 500 | Object/subject-under-test measurement system (FIGS. 5A and 5B) |
| 511 | Area-under-inspection |
| 550 | Measurement module |
| 560 | Carrier/housing for measurement module |
| 570 | Object-under-test (FIG. 5A, general case, FIG. 5B, mammalian tooth, et al.) |
| 580 | Defect on object-under-test |
| 700 | Patterned optic implementation |
| 705 | Base pattern intensity versus position profile |
| 710 | Profile intensity pattern |
| 750 | Equation for base intensity pattern versus position (Eqn (8)) |
| 500.1 | Architecture for taking Object-under-test measurement at time t1 |
| 500.2 | Architecture for taking Object-under-test measurement at time t2 |
| 500.3 | Architecture for taking Object-under-test measurement at time t3 |
| 500.4 | Architecture for taking Object-under-test measurement at time t4 |
| 511 | Area under inspection by first portion of camera at time t1 |
| 512 | Area under inspection by second portion of camera at time t1 |
| 513 | Area under inspection by third portion of camera at time t1 |
| 514 | Area under inspection by fourth portion of camera at time t1 |
| 521 | Area under inspection by first portion of camera at time t2 |
| 522 | Area under inspection by second portion of camera at time t2 |
| 523 | Area under inspection by third portion of camera at time t2 |
| 524 | Area under inspection by fourth portion of camera at time t2 |
| 531 | Area under inspection by first portion of camera at time t3 |
| 532 | Area under inspection by second portion of camera at time t3 |
| 533 | Area under inspection by third portion of camera at time t3 |
| 534 | Area under inspection by fourth portion of camera at time t3 |
| 541 | Area under inspection by first portion of camera at time t4 |
| 542 | Area under inspection by second portion of camera at time t4 |
| 543 | Area under inspection by third portion of camera at time t4 |
| 544 | Area under inspection by fourth portion of camera at time t4 |
| 550 | Measurement module (either 400, 900) |
| 560 | Carrier/housing for measurement module |
| 570 | Object-under-test (FIGS. 5.1A-5.4A general case, FIGS. 5.1B-5.4B pipeline) |
| 580 | Defect on object-under-test (FIGS. 5.1A-5.4A general, FIGS. 5.1B-5.4B pipeline) |

| Reference numeral | component/feature description |
|---|---|
| 590 | Particle flowing within fluid-under-test (FIGS. 5.1B-5.4B pipeline embodiment) |
| 595 | Direction of motion (FIGS. 5.1A-5.4A general case, FIGS. 5.1B-5.4B pipeline) |
| 600 | Patterned optic implementation |
| 605 | Base pattern intensity versus position profile |
| 610 | Phase One intensity pattern |
| 620 | Phase Two intensity pattern |
| 630 | Phase Three intensity pattern |
| 640 | Phase Four intensity pattern |
| 650 | Base pattern intensity versus position equation] |
| 700 | Alternate patterned optic implementation |
| 705 | An alternate base pattern intensity versus position profile |
| 710 | An alternate intensity pattern |
| 750 | An alternate equation for base intensity pattern versus position |
| 800 | Oil (or other fluid) pipeline measurement at time t4 |
| 811 | Area under inspection by first portion of camera at time t1 |
| 812 | Area under inspection by second portion of camera at time t1 |
| 813 | Area under inspection by third portion of camera at time t1 |
| 814 | Area under inspection by fourth portion of camera at time t1 |
| 850 | Ring measurement module configuration |
| 860 | Carrier for measurement module |
| 861 | Rear annulus for stabilizing rear of measurement module carrier and establishing thrust from flow |
| 862 | Front annulus for stabilizing rear of measurement module carrier and establishing thrust from flow |
| 863 | Another front annulus for stabilizing rear of measurement module carrier and establishing thrust from flow |
| 870 | Bottom of pipeline wall (6 O'Clock position) |
| 871 | Top of pipeline wall (12 O'Clock position) |
| 880 | Defect on oil pipeline wall |
| 885 | Oil |
| 890 | Particle floating in the oil |
| 895 | Direction of motion |
| 900 | Ring measurement module |
| 910 | Projection system |
| 920 | Single camera system |
| 930 | Measurement module mechanical mount and cooling system |
| 945 | Projector illumination area |
| 946 | Camera field of view |
| 950 | Measurement module thermal isolation chamber |
| 955 | System controller and data storage thermal isolation chamber |
| 960 | System controller |
| 970 | Data storage |
| 970 | Bottom of pipeline wall (6 O'Clock position) |
| 971 | Top of pipeline wall (12 O'Clock position) |
| 980 | System controller and data storage mechanical mount and cooling system |
| 985 | Control and data bus |
| 990 | Projector aperture |
| 995 | Camera aperture |

One aspect of the invention includes a compact system 400 employing: a light source 410; an Illumination optical system 420 (comprising a plurality of lens elements) in front of a unique fixed-pattern optic 430 from which a superimposed/overlaid SLI pattern such as 600, 710 (composed of a plurality of SLI patterns) is output 435 to illuminate a surface of a 3-D object/subject-under-test (e.g., 570, 870) or area-under-inspection (e.g., 511-514, 811-814), as the case may be; and a Projection optical system 440 (comprising a plurality of lens elements downstream of fixed-pattern optic 430). A second related aspect of the invention includes a method that eliminates the need for complex traditional phase unwrapping algorithms for 3-D measurements based on SLI; the method incorporates operation of the unique fixed-pattern optic 430 from which a superimposed/overlaid SLI pattern (composed of a plurality of SLI patterns) is output 435 to illuminate a surface of a 3-D object/subject-under-test (e.g., 570, 870) or area-under-inspection (e.g., 511-514, 811-814), as the case may be. SLI 'phase unwrapping algorithms' are traditionally required and used to enable positioning of precise measurements within a larger field of view.

As noted above and detailed further in Provisional Application '626 and Util App '607, the two examples set forth in Sections A. and B. of the new multi-frequency patterns disclosed in Provisional Application '626 were introduced in terms of analogies to traditional electrical circuitry signal/current propagation types: An AC flavor and DC flavor. These same Sections A. and B. were integrated into applicants' Provisional Application No. 61/413,969 filed 15 Nov. 2010, incorporated herein by reference as noted above. The multi-frequency pattern detailed in Section A. fashioned after principals governing AC electrical systems was coined "Dual-frequency Phase Multiplexing" (DFPM). As noted in applicants' Provisional Application No. 61/413,969, the material in Section A. was earlier published as 1 Mar. 2010/Vol. 18, No. 5/Optics Express 5233 and is noted in the section of Util App '607 labeled EXAMPLE 01. The multi-frequency pattern detailed in Section B. fashioned after principals governing DC electrical systems was coined "Period Coded Phase Measuring" (PCPM). Dual-frequency Phase Multiplexing (DFPM) patterns comprise two superimposed sinusoids, one a unit-frequency phase sine wave and the other a high-frequency phase sine wave, whereby after receiving/acquiring the pattern data by an image sensor, the phase of the two patterns is separated. The unit-frequency phase is used to unwrap the high-frequency phase. The unwrapped high-frequency phase is then employed for 3-D reconstruction. Period Coded Phase Measuring (PCPM) patterns—fashioned after DC current propagation—are generated with the period information embedded directly into high-frequency base patterns, such that the high-frequency phase can be unwrapped temporally from the PCPM patterns.

The module and system of the invention employs a fixed-pattern optic 430 that has multiple sine wave patterns overlaid, i.e., superimposed, into a resultant SLI pattern such as is described in Section A and Section B, of applicants' Provisional Application No. 61/413,969. And more-particularly, the fixed-pattern optic is preferably adapted to project—as detailed above and in Util App '607 and represented at 1100 in FIG. 10—a multi-frequency pattern comprising a plurality of pixels representing at least a first and second superimposed sinusoid projected simultaneously, each of the sinusoids represented by the pixels having a unique temporal frequency and each of the pixels projected to satisfy $$I_n^p = A^p + \sum_{k=1}^{K} B_k^p \cos\left(2\pi f_k y^p + \frac{2\pi k n}{N}\right) \quad \text{Eq. (1.1)}$$

where $I_n^p$ is the intensity of a pixel in the projector for the $n^{th}$ projected image in a particular instant/moment in time (p, to represent projector); K is an integer representing the number of component sinusoids (e.g., K=2 for a dual-frequency sinusoid pattern, K=3 for a triple-frequency sinusoid, and so on), each component sinusoid having a distinct temporal frequency, where $K \leq (N+1)/2$.

Where pixels are projected to satisfy Eq. 1.1, the pixels of the images then captured by the camera are defined according to the unique technique governed by the expression:

$$I_n^c = A^c + \sum_{k=1}^{K} B_k^c \cos\left(2\pi f_k y^p + \frac{2\pi k n}{N}\right) + \eta \qquad \text{Eq. (1.2)}$$

The term η ("eta") represents a noise due to a certain amount of error introduced into the image by the light sensor of the camera. To obtain phase terms from the pixels projected in accordance with Eq. 1.2, the unique expression, below, is carried-out for each k:

$$2\pi f_k y^p = \arctan\left(\frac{\sum_{n=0}^{N-1} I_n^c \times \cos\left(\frac{2\pi k n}{N}\right)}{\sum_{n=0}^{N-1} I_n^c \times \sin\left(\frac{2\pi k n}{N}\right)}\right) \qquad \text{Eq. (1.3)}$$

where, as before, $y^p$ represents a spatial coordinate in the projected image.

When applying the use of temporal unwrapping techniques, for the case where k=2 using Eq. 1.1, one can determine that the projected pixels will satisfy $$I_n^p = A^p + B_2^p \cos\left(2\pi f_2 y^p + \frac{2\pi 2n}{N}\right), k = 2 \qquad \text{Eq. (1.1)}$$

A second set of patterns (k=1) all unit-frequency sinusoids (i.e., f=1) is superimposed with a high-frequency sinusoid, such as one of 20 stripes, k=2 pattern. The unit-frequency signal is defined by an adaptation of Eq. 1.1

$$I_n^p = A^p + B_1^p \cos\left(2\pi f_2 y^p + \frac{2\pi n}{N}\right), k = 1 \qquad \text{Eq. (1.1)}$$

Therefore, rather than projecting a total of N patterns onto the contoured surface-of-interest, there are now 2*N patterns projected (such that K=2 and each pixel projected from the projector is comprised of a dual-frequency pattern, one is a unit-frequency sinusoid and the second is a high-frequency sinusoid).

To carry-out phase unwrapping of the high-frequency sinusoid the following steps can be taken:

$$unitPhase = \arctan\left(\frac{\cos \Sigma K_1}{\sin \Sigma K_1}\right)$$

$$highPhase = \arctan\left(\frac{\cos \Sigma K_2}{\sin \Sigma K_2}\right)/f_2$$

$$tempPhase = \text{round}\left(\frac{(unitPhase - highPhase)}{(2\pi)f_2}\right)$$

$$finalPhase = tempPhase + highPhase * (2\pi/f_2)$$

Or, summarized in pseudo code short-hand notation as done in FIG. 19, the above computational steps may be rewritten as:
 unitPhase=arctan(cosSumK1/sinSumK1);
 highPhase=arctan(cosSumK2/sinSumK2)/F2;
 tempPhase=round((unitPhase-highPhase)/(2*PI)*F2);
 finalPhase=tempPhase+highPhase*2*PI/F2

The first and second superimposed sinusoid may comprise, for example, a unit-frequency sinusoid (having a magnitude value of 1) superimposed on a high-frequency sinusoid, the unit-frequency sinusoid and high-frequency sinusoid being projected simultaneously over a selected epoch/duration of frames, n, as a plurality of pixels such that each of the pixels projected satisfy the expression 750, FIG. 6, below $$I_n^p = A^p + B_1^p \cos\left(2\pi f_h y^p - \frac{2\pi n}{N}\right) + B_2^p \cos\left(2\pi f_u y^p - \frac{4\pi n}{N}\right)$$

where $I_n^p$ is the intensity of a pixel in the projector, $A^p$, $B_1^p$, and $B_2^p$ are constants set such that the value of $I_n^p$ falls between a target intensity range, (e.g., between 0 and 255 for an 8-bit color depth projector), $f_h$ is the high frequency of the sine wave, $f_u$ is the 'unit' frequency of the sine wave. The unit-frequency signal/sinusoid is used during a demodulation step to produce a decodable, unwrapped-phase term temporally.

Additionally, the process includes a decoding of the projected patterns by carrying-out a lookup table (LUT)-based processing of video image data acquired by at least one image-capture device. The decoding step is performed to extract, real-time, coordinate information about the surface shape-of-interest. The LUT-based processing includes the step of implementing (or, querying) a pre-computed modulation lookup table (MLUT) to obtain a texture map for the contoured surface-of-interest and implementing (or, querying) a pre-computed phase lookup table (PLUT) to obtain corresponding phase for the video image data acquired of the contoured surface-of-interest. Furthermore, use of conventional digital image point clouds can be made to display, real-time, the data acquired.

Figure 6:
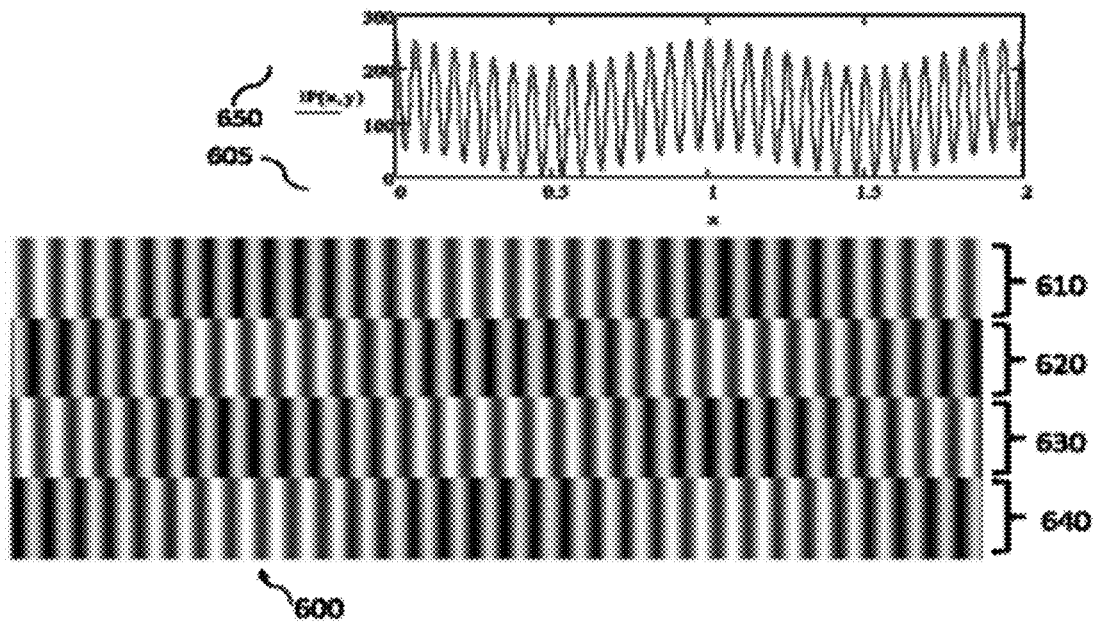
FIG. 6 A graphical representation of Profile pixel intensity pattern 600 composed of four strips 610, 620, 630, 640 of a SLI pattern, wherein each strip is offset by phase and labeled as detailed elsewhere.
Figure 7:
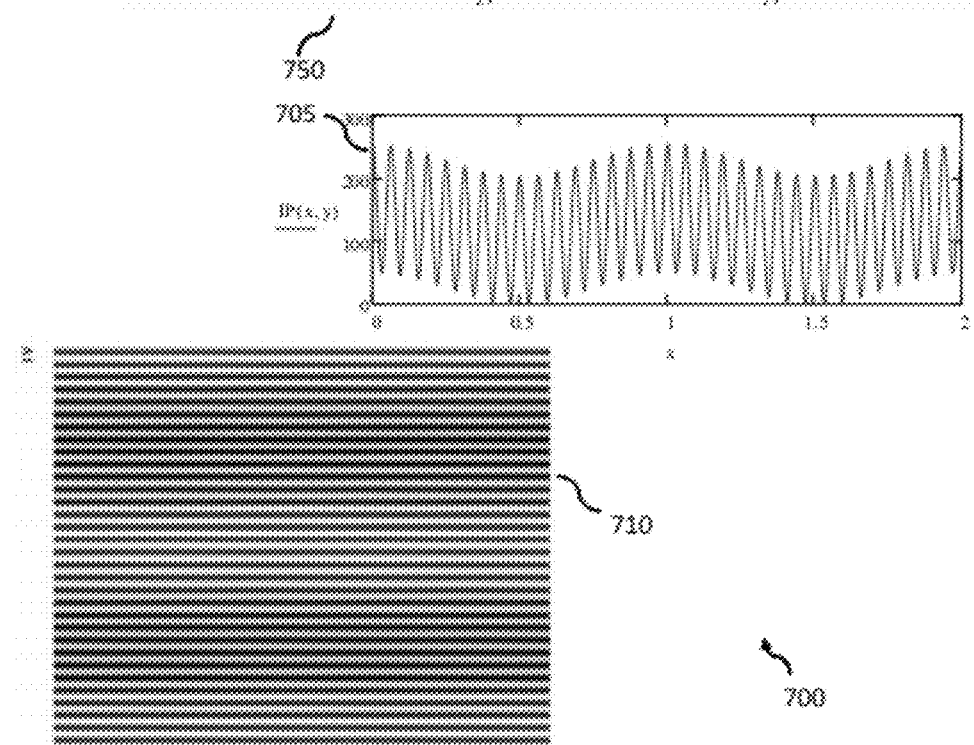
FIG. 7 Graphical representations of a Profile pixel intensity pattern 710 and base pattern intensity shown as a function of position profile 705, along with an Equation/expression 750.
Figure 10:
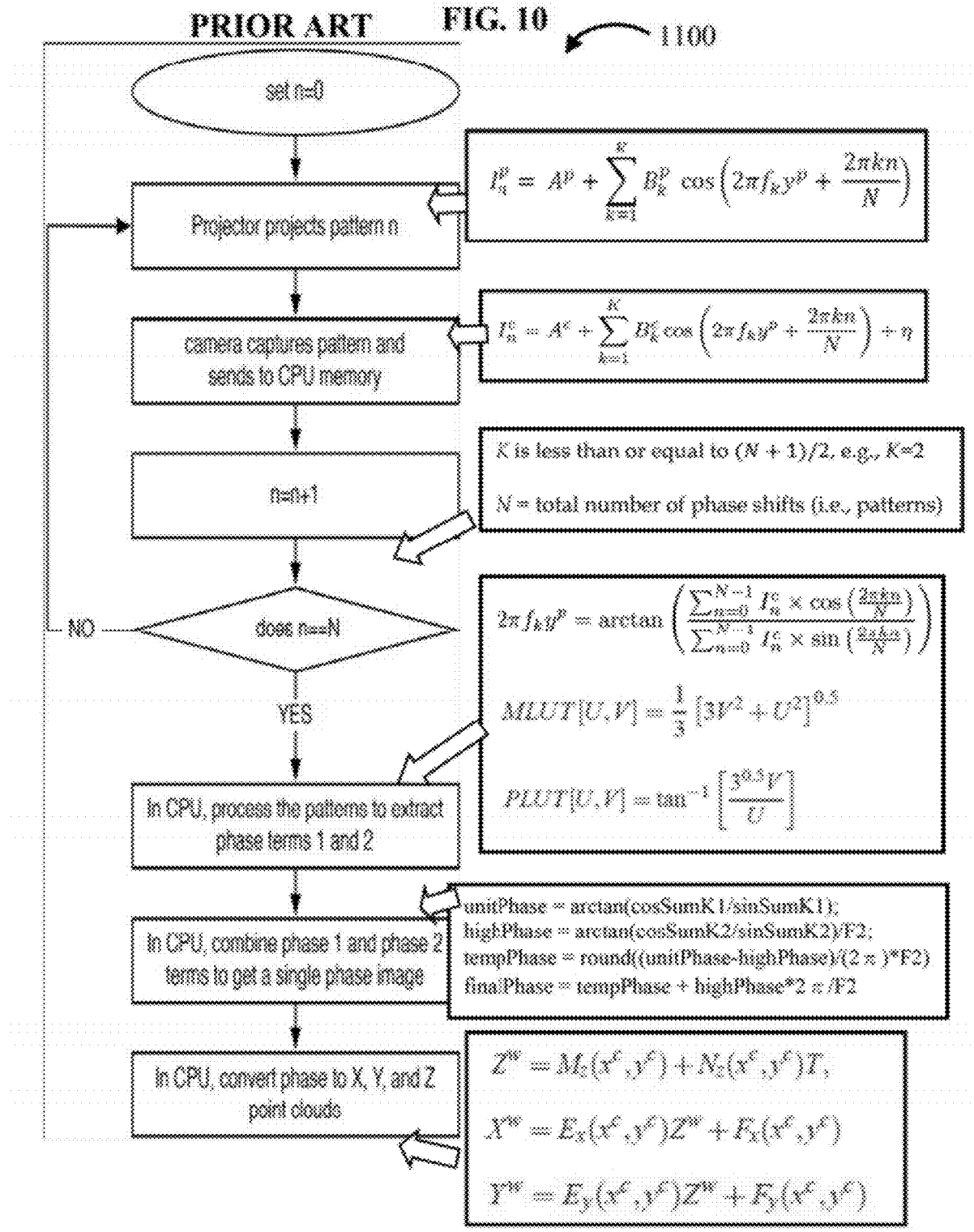
FIG. 10 A high level flow diagram (labeled PRIOR ART) depicting the unique technique 1100—disclosed in Provisional Application '626 and Util App '607—leveraged by the compact measurement apparatus and system of the invention.

Therefore, the fixed-pattern optic may be adapted to project—as detailed and represented in FIGS. 6 and 7 respectively at 650, 750, and further shown at 1100 in FIG. 10—a multi-frequency pattern characterized as having two stages. The first being a dual-frequency pattern generation and projection stage, the dual-frequency pattern characterized by the expression, below $$I_n^p = A^p + B_1^p \cos\left(2\pi f_h y^p - \frac{2\pi n}{N}\right) + B_2^p \cos\left(2\pi f_u y^p - \frac{4\pi n}{N}\right)$$

where $I_n^p$ is the intensity of a pixel in the projector, $A^p$, $B_1^p$, and $B_2^p$ are constants that are preferably set, by way of example, to make the value of $I_n^p$ fall between 0 and 255 for an 8-bit color depth projector, $f_h$ is the high frequency of the sine wave, $f_u$ is the unit frequency of the sine wave and equals 1, n represents phase-shift index, and N is the total number of phase shifts and is preferably greater than or equal to 5. The second stage comprises a de-codification stage employing a lookup table (LUT) method for phase, intensity/texture, and depth data. By way of using lookup tables (LUT) to obtain modulation (M) and phase (P) according to $$MLUT[U, V] = \frac{1}{3}[3V^2 + U^2]^{0.5} \text{ and}$$

$$PLUT[U, V] = \tan^{-1}\left[\frac{3^{0.5} V}{U}\right].$$

Thereafter, a conversion of phase to X, Y, Z point clouds is implemented using the expressions:

$$Z^w = M_z(x^c, y^c) + N_z(x^c, y^c)T,$$

$$X^w = E_x(x^c, y^c)Z^w + F_x(x^c, y^c)$$

$$Y^w = E_y(x^c, y^c)Z^w + F_y(x^c, y^c)$$

Further details concerning solutions and use of the three expressions above can be found elsewhere herein and in Util App '607.

Effectively identical expressions 650, 750 (FIGS. 6 and 7) define a profile pattern of pixel intensity (600, 710) for use with the fixed-patterned optic 430 (FIG. 4). Preferably, pixel intensity profile pattern 600, 710 is 'fixed' into a transparent lens member, by way of etching into, depositing onto, or otherwise 'fixing' into a transparent lens member, causing light entering the patterned optic 430 to exit as pattern light output 435 having the intended pixel intensity profile pattern 600, 710. As a result, the projected pattern (physically etched or deposited onto a transparent lens member) is comprised of, for example, a high frequency sine wave pattern and a low frequency sinewave pattern (this combination of sine waves is graphically represented at 605, FIGS. 6 and 705, FIG. 7). The high frequency pattern enables precise measurement of the 3-D shape of objects. The low frequency pattern enables course measurement of the distance between the object under test and the measurement system. As mentioned elsewhere, this eliminates the conventional employment of additional, sophisticated computer processing required when applying phase unwrapping algorithms. The low frequency measurement provides a rough (course) estimate of the 3-D coordinates of a measured point. The high frequency measurement precisely locates the point (fine measurement).

Figure 2:
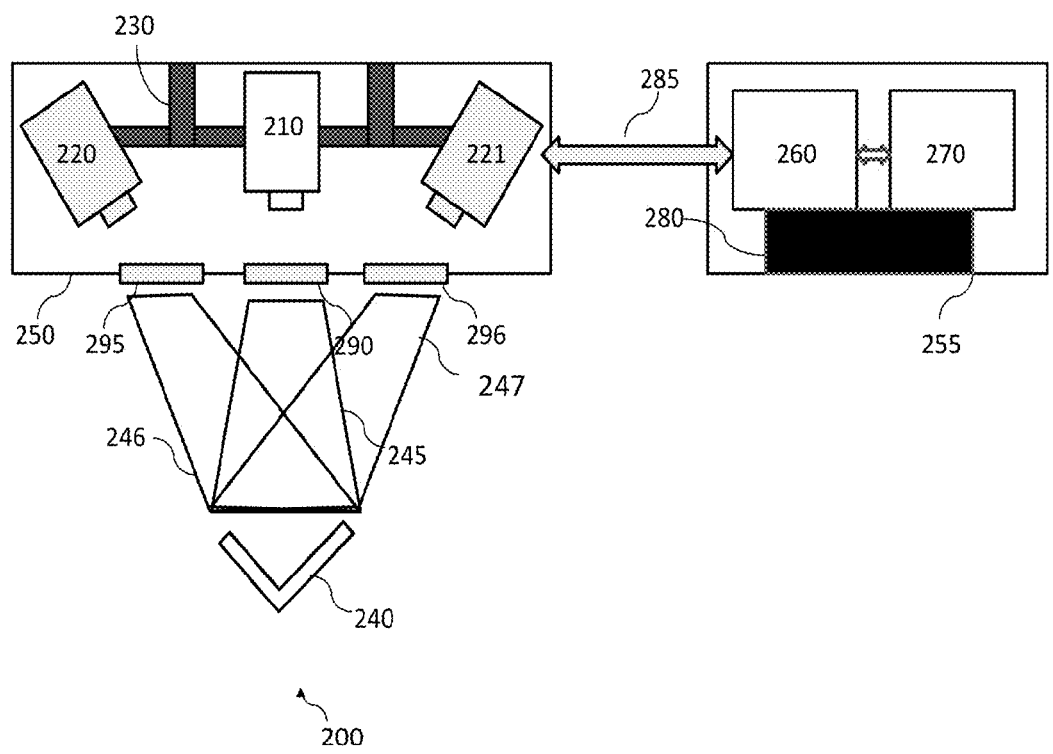
FIG. 2 A high-level schematic illustrating a second Measurement module 200 in communication with a System controller and data storage case/housing 255 enclosing a System controller 260 and the Data storage 270.

Once again, the high-level block diagram in FIG. 1 schematically illustrates a Measurement module 100 having Measurement module thermal isolation chamber/case 150 enclosing a Projection system 110 and single camera system 120, in communication with a System controller and data storage case/housing 155 enclosing a System controller 160 and Data storage 170. The high-level schematic in FIG. 2 illustrates a second Measurement module 200 in communication with a System controller and data storage case/housing 255 enclosing a System controller 260 and the Data storage 270. The high-level block diagram in FIG. 3 schematically illustrates a Camera system 300 for capturing an image of the illuminated Object/subject-under-test 570, FIGS. 5A and 5B. Camera system 300 has an Image sensor 310, Camera lens 320 comprising Camera lens elements (generally labeled 321), Camera pixel data processing device 370, Camera pixel data output bus 365, and means for connection to Camera power 350.

The high-level block diagram in FIG. 4 schematically illustrates Projection system architecture 400 having a Light source 410, optical system 420, Fixed-pattern optic 430 in communication with an Optic shifting element 431 (for shifting, or reorienting, the fixed-pattern optic structure 430), and Projection optical system 440.

The high-level block diagrams in FIGS. 5.1A-5.4A schematically illustrate a Measurement module 550 (general case) in operation measuring, respectively, Area(s)-under-inspection 511-514, 521-524, 531-534, 541-544 within which an Object-under-test 570 (having a defect 580) is being investigated by the Measurement module 550. Direction arrow 595 represents the relative linear motion between module 550 and Object-under-test 570 such that defect 580 under Measurement module 550 moves into a new Area-under-inspection 511, 512, 513, 514 with-respect-to the four fixed-pattern phases: 610, 620, 630, 640 (see FIG. 6). As labeled, the pattern projected on first Area-under-inspection 511 at time "t1" (FIG. 5.1A) results from light that passes through the Phase One intensity pattern 610 portion of the fixed-pattern optic 430. The pattern projected on second Area-under-inspection 512 at time "t2" (FIG. 5.2A) results from light that passes through the Phase Two intensity pattern 620 portion of the fixed-pattern optic 430, and so on.

An alternative embodiment of the Measurement module 550 is depicted in FIGS. 5.1B-5.4B highlighting the case where an Object-under-test 570, 571 comprises the inside wall of a pipeline or tubing (570, 571 representing cross-sections thereof), within which a fluid (non-compressible fluids, such as oil or water, or compressible fluids, such as natural gas) can flow; wall-under-test 570 is shown, by way of example, with defect 580 (representing as a small area of decay such as a fracture, fission, crack(s), etc.) in Wall-under-test 570. Also shown is a Particle 590 flowing within the fluid-under-test between walls 570, 571. In a manner similar to FIGS. 5.1A-5.4A, shown is a Measurement module 550 adapted/retrofitted for moving along walls 570, 571. In operation, as shown in FIGS. 5.1B-5.4B module 550 moves along walls 570, 571 measuring Area(s)-under-inspection, respectively, 511-514, 521-524, 531-534, 541-544. Direction arrow 595 represents the relative linear motion between module 550 and Wall-under-test 570 such that defect 580 moves into a new Area-under-inspection 511, 512, 513, 514 with-respect-to module 550. As labeled, the pattern projected on first Area-under-inspection 511 at time "t1" (FIG. 5.1B) results from light that passes through the Phase One intensity pattern 610 portion of the fixed-pattern optic 430. The pattern projected on second Area-under-inspection 512 at time "t2" (FIG. 5.2B) results from light that passes through the Phase Two intensity pattern 620 portion of the fixed-pattern optic 430, and so on, for FIGS. 5.3B, 5.4B.

FIG. 6 includes a graphical representation of Profile pixel intensity pattern 600 composed of four strips 610, 620, 630, 640 of a SLI pattern, wherein each strip is offset by phase and labeled as follows: Phase One intensity pattern 610, Phase Two intensity pattern 620, Phase Three intensity pattern 630, and Phase Four intensity pattern 640; and, a graphical representation of base pattern intensity shown as a function of position profile 605, along with an Equation/expression 650 for base intensity pattern as a function of position. FIG. 7 includes graphical representations of a Profile pixel intensity pattern 710 and base pattern intensity shown as a function of position profile 705, along with an Equation/expression 750 for base intensity pattern as a function of position.

Figure 8:
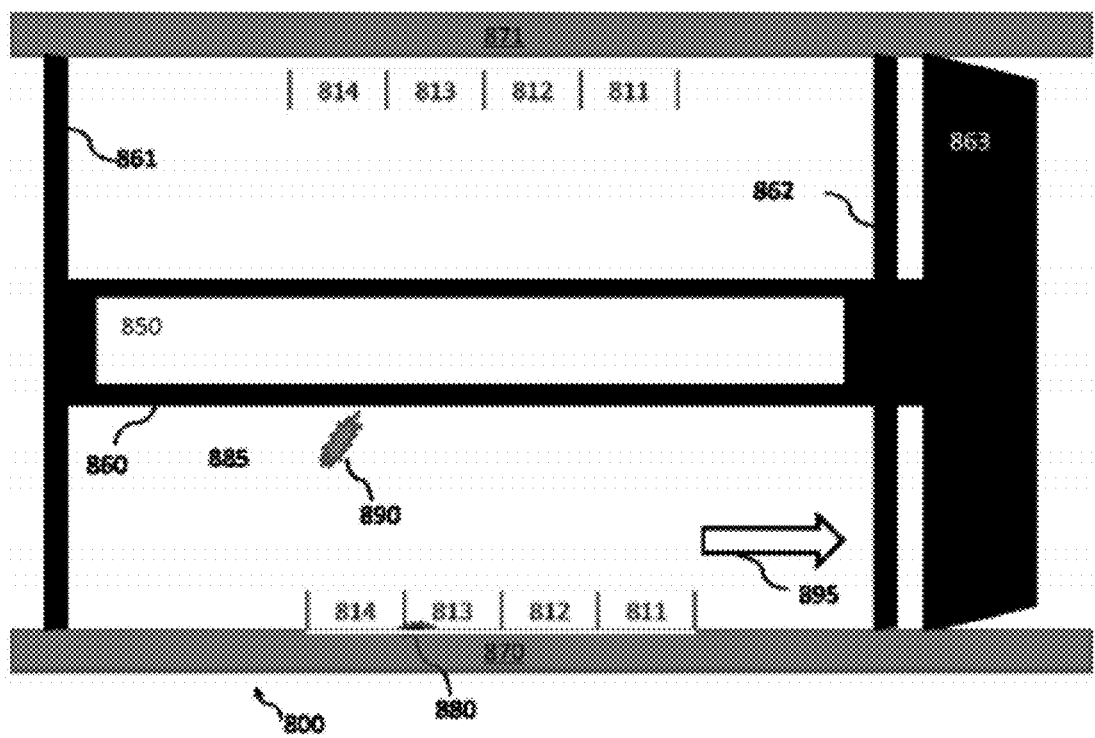
FIG. 8 A high-level block diagram similar to FIG. 5.3B, representing an implementation of an alternative embodiment of the invention wherein a defect 880 is shown on the object-under-test 870.

The high-level block diagram of FIG. 8, similar to FIG. 5.3B, represents an implementation of an alternative embodiment of the invention wherein a defect 880 is shown on the object-under-test 870 (here, the object-under-test are walls 870, 871 of a pipeline/piping) and a particle 890 is shown floating within the fluid flowing along pipeline 870, 871.

Figure 9:
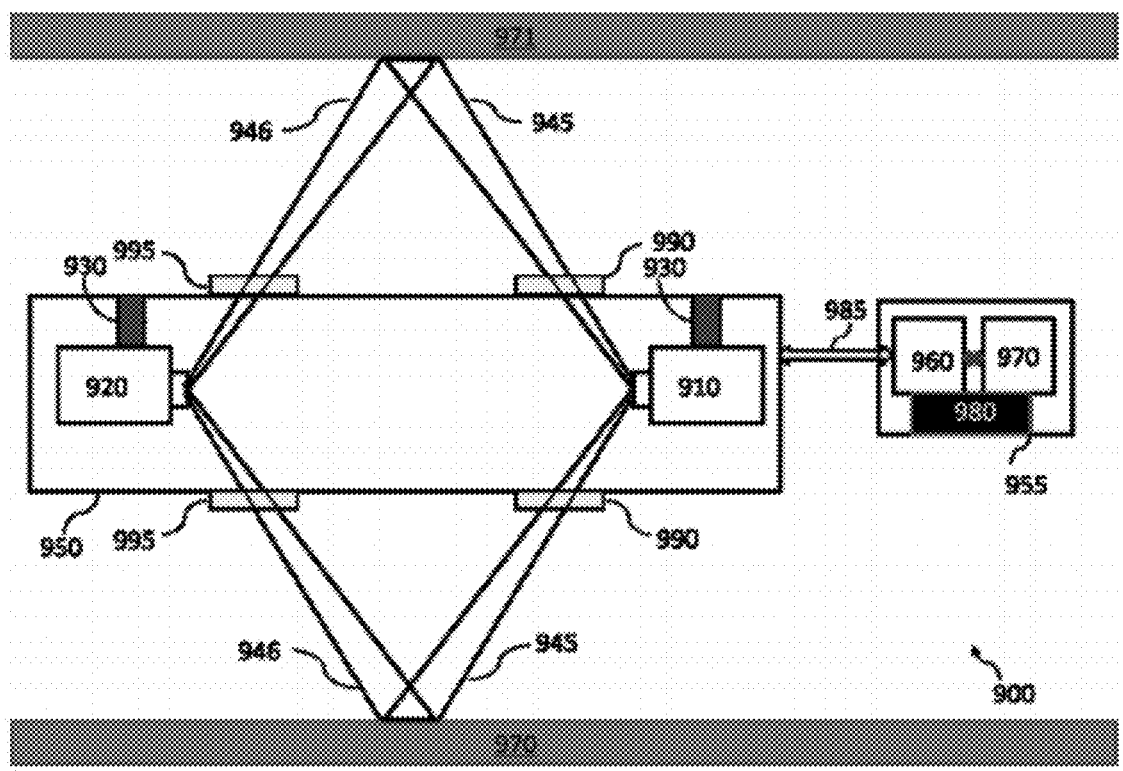
FIG. 9 Depicting certain features akin to those illustrated by the block diagrams of FIGS. 1 and 2, FIG. 9 schematically illustrates an alternative Measurement module 900.

Depicting certain features akin to those illustrated by the block diagrams of FIGS. 1 and 2, FIG. 9 schematically illustrates an alternative Measurement module 900 having Measurement module thermal isolation chamber/case 950 enclosing a Projection system 910 and single camera system 920, in communication with a System controller and data storage case/housing 955 enclosing a System controller 960 and Data storage 970.

Returning, now, to FIG. 1: This diagram illustrates one embodiment of the Measurement module, 100, comprising a Projection system 110, a Single camera system 120, a Measurement module mechanical mount and cooling system 130, a Measurement module thermal isolation chamber/case 150, a System controller and data storage case 155, a System controller 160, Data storage 170, a System controller and data storage mechanical mount and cooling system 180, a Control and data bus 185, a Projector aperture 190, and a Camera aperture 195.

The Projection system 110 projects a pattern through the Projector aperture 190 that is focused onto the object-under-test 570, 870 (FIGS. 5.1A-5.4A, 5.1B-5.4B, and 8) and creates a Projector illumination area 145. The pattern is distorted by the shape of the object according to the object's 3-D characteristics. Provided the distorted pattern is within the Camera field of view 146, the distortions are recorded by the Single camera system 120 which observes the object under test through the Camera aperture 195. Only portions of the object under test within the Projector illumination area 145 and within the Camera field of view 146 can be measured. The Projection system 110 and the Single camera system 120 are held in place with an assembly labeled 130 which uniquely incorporates within Measurement module 100 the functionalities of Measurement module mechanical mount and cooling system. In order to ensure suitably accurate 3-D measurements, a Calibration fixture 140 is used to precisely establish the relative physical positions of the Projection system 110 and the Single camera system 120. Since the physical shape of the Measurement module mechanical mount and cooling system, 130, will change a result of environmental conditions (i.e., physical dimensions of 130 will expand and contract slightly with temperature changes), a pre-calibration of the Measurement module 100 using the Calibration fixture 140 is done over a wide range of environmental conditions. Pre-calibration is preferably done under controlled environment, prior to monitoring of an object-under-test 570.

For example, a temperature range from 31 40 C to 120 C might be used during pre-calibration of the Measurement module 100. Calibration data, along with measurement results, are stored in Data storage 170 by the System controller 160. Data and control information are passed between the Projection system 110, the Single camera 120 and the System controller 160 via the Control and data bus 185. The System controller and data storage case 155 maintains the System controller 160 and the Data storage 170 within their respective operating temperatures ranges. The Measurement module thermal isolation chamber/case 150, along with the Measurement module mechanical mount and cooling system 130, aids in maintaining the Projection system 110 and the Single camera system 120 within respective target operating temperature ranges.

An alternative preferred embodiment of the invention is shown in FIG. 2. In this embodiment, the Projection system 210 projects a pattern through the Projector aperture 190 that is focused onto the object-under-test (e.g., at 570, FIGS. 5.1A-5.4A, 5.1B-5.4B, or at 870, FIG. 8) producing a Projector illumination area defined at 245. The resultant pattern illuminating an object-under-test (570, 870) becomes distorted by the shape of the object according to the object's 3-D surface characteristics. Provided the distorted pattern is within a composite Camera field of view 246 of the First and Second Camera Systems 220 and 221, the distortions are recorded by the Camera systems 220, 221. Only portions of the object-under-test within the Projector illumination area defined at 245 and, at the same time, within the composite Camera field of view 246 will be measured. The Projection system 210 and Single camera system 220 are held in place using the Measurement module mechanical mount and cooling system 230. In order to ensure accurate 3-D measurements, a Calibration fixture 240 is used to precisely establish relative physical positions of (or, relative distances between) the Projection system 210 and First Camera System 220 and the projection system 210 and Second Camera System 221. Because the Measurement module mechanical mount and cooling system 230 will change shape (even if only a slight difference in original dimensions) as a result of environmental conditions, a calibration of the Measurement module 200 using the Calibration fixture 240 is done over a wide range of environmental conditions prior to placing the Measurement module in operation.

For example, a temperature range from −40 C to 120 C might be used during calibration of the Measurement module 200. Calibration data, along with measurement results, are stored in Data storage 270 by the System controller 260. Data and control information are passed between the Projection system 210, the First Camera System 220, the Second Camera System 221 and the System controller 260 via the Control and data bus 285. The System controller and data storage case 255 maintains the System controller 260 and the Data storage 270 within their respective operating temperatures ranges. The Measurement module thermal isolation chamber/case 250 combined with the Measurement module mechanical mount and cooling system 230 maintain the Projection system 210 and the Single camera system 220 within a respective target operating temperature range.

Embodiments of the Projection system 110 (as well as alternative Projection system labeled 210, FIGS. 2 and 910, FIG. 9) are discussed, next, in connection with Projection system architecture 400, FIG. 4 (further discussion of embodiments depicted in FIGS. 5.1B-5.4B, 8 and 9 are found under "EXAMPLES|alternative useful structures"). Projection system architecture 400 includes a Light source 410 for producing a light emission 415 incident upon an Illumination optical system 420 having first and second Illumination system lens elements 421, 422 whose output is focused on the Patterned optic 430 which, in turn, produces the Patterned light output 435. Patterned light output 435 is then focused by the Projection optical system 440 onto the object-under-test (e.g., at 570, FIGS. 5.1A-5.4A, 5.1B-5.4B, or at 870, FIG. 8). As depicted in the schematics of FIG. 4, Projector power 450 supplies power to elements of 400 of projection system 110, FIG. 1 or 910, FIG. 9.

Embodiments of the Fixed-pattern optic 430 are illustrated in FIGS. 6 and 7 (respectively at 600, 710). The graphic representations in FIG. 6 and those in FIG. 7, each collectively represent alternative Patterned optic implementations for fixed-pattern optic 430. Preferably, as mentioned elsewhere, fixed-pattern optic 430 is comprised of a glass substrate on which a reflective material is etched, deposited, or otherwise 'fixed' to the glass substrate (transparent lens member), such that the transmittance of light through the patterned optic results in the Profile intensity pattern labeled 600, 710. The Base pattern intensity vs. position profile at 605, 705 are each graphical representations of the Equation for base intensity pattern vs. position 650, 750, identified and further explained elsewhere herein.

FIGS. 5.1A-5.4A, as well as the embodiment represented in FIGS. 5.1B-5.4B, illustrate respective implementations 500.1, 500.2, 500.3, 500.4 of a Measurement Module 100, 200, 900 in operation while taking a measurement of an Object-under-test 570 (labeled in the embodiments shown in FIGS. 5.1A-5.4A and in FIGS. 5.1B-5.1B). The Object-under-test 570 is shown with a Defect on the object under test 580 and with a Direction of motion 595 relative to the measurement system. Measurements of the object-under-test 570 will occur within that area where the projected image and the camera field of view overlap.

In FIGS. 5.1A and 5.1B at 500.1, the Measurement Module 550 is shown located inside a Carrier/housing for the measurement module 560. As shown in the embodiment 500.1 of FIG. 5.1B, attached to the Carrier/housing 560 is a Rear annulus for stabilizing rear of measurement module carrier and establishing thrust from flow 561, a Front annulus for stabilizing rear of measurement module carrier and establishing thrust from flow 562, and a Second front annulus for stabilizing rear of measurement module carrier and establishing thrust from flow 563. The combination of 561, 562, and 563 stabilize the motion of the 560 and ensure that 560 moves with the flow rate of the Material 585, gas or liquid, that is inside the pipeline. Measurement of the pipeline wall will occur on all surfaces. 571 is the Top of the pipeline wall, herein referred to as the 12 O'Clock position. 570 is the Bottom of the pipeline wall, herein referred to as the 6 O'Clock position. The Measurement module 550 will differentiate between a Particle 590 floating in the fluid (a compressible fluid such as natural gas, or a non-compressible, such as oil or water) within pipeline walls 570, 571 and a Defect 580. Differentiation is done by means of the distance of the particle of defect from the measurement module. This distance relates directly to the measured phase. To streamline the measurement process, a phase threshold can be established. The phase threshold can be defined to be the zero phase position. Particles and defects with positive phase are then captured; those with negative phase are ignored (or vice versa).

In the embodiment of 500.1 using pattern 600 (FIG. 6), the pattern projected on Area-under-inspection by first portion of camera at time t1 (this Area-under-inspection is 511) results from light that passes through the Phase One intensity pattern 610 portion of the Patterned optic 430. Thus, the Defect 580 is illuminated with a Phase One intensity pattern 610 and inspected by the camera system. Because the Object-under-test 570 moves in the Direction of motion 595, after a certain time, which is based on the velocity of the Object-under-test 570, the Carrier/housing 560 will have moved such that the Defect 580 is illuminated by the Phase Two intensity pattern 620. The embodiment labeled 500.2 illustrates this case (i.e., illuminating Area-under-test 512 with 620). Through successive motion, likewise illustrated at 500.3 and 500.4 (FIGS. 5.3A and 5.4A as well as FIGS. 5.3B and 5.3B), the Object-under-test 570 moves such that the Defect 580 is illuminated and observed, respectively, through Phase Three intensity pattern 630 and Phase Four intensity pattern 640. As a result, measurement of the Defect 580 with a four phase PMP pattern is achieved.

The Measurement module 550 measures an Area-under-inspection 511, as shown in FIGS. 5A and 5B. An Object-under-test 570 is within the Area-under-inspection 511. The Object-under-test 570 is first illuminated with the Profile intensity pattern 710. Once the camera system (for example, that shown as 300 in FIG. 3), has captured an image of an Object-under-test 570 undergoing illumination with Profile intensity pattern 710, the Patterned optic shifting element 431 acts on the fixed-pattern optic 430 to shift the pattern spatially by, for example, 90 degrees of the fine pitch pattern. In this manner, the fixed-pattern optic 430 is shifted according to the high frequency cosine function in Equation/expression 750. Expression 750 represents the relationship between base intensity pattern vs. position.

As also explained elsewhere: The module and system of the invention employs a fixed-pattern optic 430 that has multiple sine wave patterns overlaid, i.e., superimposed, into a resultant SLI pattern such as is described in Section A, of applicants' Prov App No. 61/413,969; a special case of which—when one sinusoid of the multi-frequency pattern is set to unit magnitude—is reflected in expression 750 (identical to 650). Other shifts are contemplated hereby: Shifting the fixed-pattern optic 430 in increments of 90 degrees is one of a multitude of contemplated embodiments. Shifting the fixed-pattern optic 90 degrees in separate increments—through one full 365 degree rotation—will provide 3-D measurements about targeted surfaces of an Object-under-test 570 in a manner consistent with a four PMP approach.

Examples|Alternative Useful Structures

Embodiments depicted in FIGS. 8-9. The technique and system of the invention are useful in operation to make real-time calculations of 3-D data measured with a camera from a surface of an object-under-test 870 or area-under-inspection 811-814, such as a surface within the interior of a pipeline/tubing. It is contemplated that a multitude of objects and surfaces may be inspected according to the invention. As explained elsewhere, FIG. 9 shows an alternative embodiment of the Measurement Module 900 that enables simultaneous inspection of the interior circumference of the pipeline with a single measurement module. In this embodiment, the field of view of the camera system and the projection system encompass the interior circumference of the pipeline.

While certain representative embodiments and details have been shown for the purpose of illustrating features of the invention, those skilled in the art will readily appreciate that various modifications, whether specifically or expressly identified herein, may be made to these representative embodiments without departing from the novel core teachings or scope of this technical disclosure. Accordingly, all such modifications are intended to be included within the scope of the claims. Although the commonly employed preamble phrase "comprising the steps of" may be used herein, or hereafter, in a method claim, the applicants do not intend to invoke 35 U.S.C. §112 ¶6 in a manner that unduly limits rights to its claimed invention. Furthermore, in any claim that is filed herewith or hereafter, any means-plus-function clauses used, or later found to be present, are intended to cover at least all structure(s) described herein as performing the recited function and not only structural equivalents but also equivalent structures.

We claim:

1. A surface measurement module for 3-D triangulation-based image acquisition of a subject-under-inspection and under observation by at least one camera, the module comprising:
   (a) a casing housing an optical system comprising a plurality of lens elements positioned between a fixed-pattern optic and a light source;
   (b) an output of said fixed-pattern optic comprising a multi-frequency pattern comprising a plurality of pixels representing at least a first and second superimposed sinusoid projected simultaneously, each of the sinusoids represented by the pixels having a unique temporal frequency and each of the pixels projected to satisfy $$I_n^p = A^p + \sum_{k=1}^{K} B_k^p \cos\left(2\pi f_k y^p + \frac{2\pi k n}{N}\right) \qquad \text{Eq. (1.1)}$$

where $I_n^p$ is an intensity of a pixel for an $n^{th}$ projected image in a particular moment in time; K is an integer representing a number of component sinusoids, each component sinusoid having a distinct temporal frequency, where K is less than or equal to (N+1)/2, said output comprising at least N projected patterns; a parameter $B_k^p$ represents constants that determine an amplitude or signal strength of the component sinusoids; $A^p$ is a scalar; $f_k$ is a spatial frequency of a $k^{th}$ sinusoid corresponding to temporal frequency k; and $y^p$ represents a spatial coordinate in an image projected as a result of said output;

(c) said fixed-pattern optic comprises said multi-frequency pattern fixed into a glass substrate, such that said output thereof results during said projection onto the subject-under-inspection;

(d) the subject-under-inspection and said fixed-pattern optic in motion in relative linear motion during projection onto the subject-under-inspection of said output of said fixed-pattern optic; and (e) a plurality of images captured of said output of said fixed-pattern optic during projection onto the subject-under-inspection are used for the image acquisition.

2. A system comprising the module of claim 1 positioned for inspection of a pipeline interior wall; the module further comprising a rear annulus and a front annulus for stabilizing the module within said pipeline interior during said relative linear motion.

3. A system comprising the module of claim 1 positioned within a tubing whereby the subject-under-inspection comprises an interior surface of a section of said tubing; the module further comprising a rear annulus and a front annulus for stabilizing the module within said tubing during said relative linear motion.

4. The surface measurement module of claim 1, wherein said multi-frequency pattern is fixed by etching a reflective material on said glass substrate member.

5. The surface measurement module of claim 1, wherein said multi-frequency pattern is fixed by depositing a material onto said glass substrate member.

6. A system for implementing 3-D triangulation-based image acquisition of a subject-under-inspection and under observation by at least one camera, the system comprising a surface measurement module comprising:

(a) a casing housing an optical system comprising a plurality of lens elements positioned between a fixed-pattern optic and a light source;

(b) an output of said fixed-pattern optic comprising a multi-frequency pattern comprising a plurality of pixels representing at least a first and second superimposed sinusoid projected simultaneously, each of the sinusoids represented by the pixels having a unique temporal frequency and each of the pixels projected to satisfy $$I_n^p = A^p + \sum_{k=1}^{K} B_k^p \cos\left(2\pi f_k y^p + \frac{2\pi k n}{N}\right) \qquad \text{Eq. (1.1)}$$

where $I_n^p$ is an intensity of a pixel for an $n^{th}$ projected image in a particular moment in time; K is an integer representing a number of component sinusoids, each component sinusoid having a distinct temporal frequency, where K is less than or equal to (N+1)/2, said output comprising at least N projected patterns; a parameter $B_k^p$ represents constants that determine an amplitude or signal strength of the component sinusoids; $A^p$ is a scalar; $f_k$ is a spatial frequency of a $k^{th}$ sinusoid corresponding to temporal frequency k; and $y^p$ represents a spatial coordinate in an image projected as a result of said output;

(c) the subject-under-inspection and said fixed-pattern optic in relative linear motion during projection onto the subject-under-inspection of said output of said fixed-pattern optic; and (d) a plurality of images captured of said output of said fixed-pattern optic during projection onto the subject-under-inspection are used for the image acquisition.

7. The system of claim 6, wherein the subject-under-inspection comprises a subject selected from the group consisting of: a pipeline interior wall, an interior surface of a section of tubing, a non-compressible fluid, and a compressible fluid.

8. The system of claim 6, wherein said fixed-pattern optic comprises said multi-frequency pattern fixed into a glass substrate, such that said output of said fixed-pattern optic results during said projection onto the subject-under-inspection.

9. The system of claim 6, wherein said fixed-pattern optic comprises said multi-frequency pattern fixed into a glass substrate by etching a reflective material thereon such that said output of said fixed-pattern optic results during said projection onto the subject-under-inspection.

10. The system of claim 6, wherein said fixed-pattern optic comprises said multi-frequency pattern fixed into a glass substrate by depositing a material thereon such that said output of said fixed-pattern optic results during said projection onto the subject-under-inspection.

\* \* \* \* \*